United States Patent
Higashi et al.

(10) Patent No.: US 12,410,267 B2
(45) Date of Patent: Sep. 9, 2025

(54) COMPOSITION PRODUCTION METHOD, AND COMPOSITION

(71) Applicant: DAIKIN INDUSTRIES, LTD., Osaka (JP)

(72) Inventors: Masahiro Higashi, Osaka (JP); Sumi Ishihara, Osaka (JP); Satoru Yoneda, Osaka (JP); Yosuke Kishikawa, Osaka (JP); Hirokazu Aoyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 820 days.

(21) Appl. No.: 17/606,304

(22) PCT Filed: Apr. 27, 2020

(86) PCT No.: PCT/JP2020/018041
§ 371 (c)(1),
(2) Date: Oct. 25, 2021

(87) PCT Pub. No.: WO2020/218619
PCT Pub. Date: Oct. 29, 2020

(65) Prior Publication Data
US 2022/0195080 A1 Jun. 23, 2022

(30) Foreign Application Priority Data

Apr. 26, 2019 (JP) .................. 2019-085980
Oct. 7, 2019 (JP) .................. 2019-184441
Nov. 19, 2019 (JP) .................. 2019-209162

(51) Int. Cl.
| | |
|---|---|
| C08F 214/18 | (2006.01) |
| B01D 61/14 | (2006.01) |
| B01D 61/24 | (2006.01) |
| B01D 69/02 | (2006.01) |
| C02F 1/44 | (2023.01) |
| C07C 43/17 | (2006.01) |
| C08F 16/26 | (2006.01) |

(52) U.S. Cl.
CPC ............ *C08F 16/26* (2013.01); *B01D 61/145* (2013.01); *B01D 61/243* (2013.01); *B01D 69/02* (2013.01); *C02F 1/444* (2013.01); *C07C 43/17* (2013.01); *B01D 2325/34* (2013.01)

(58) Field of Classification Search
CPC ............ C08F 216/1441; C08F 116/14; C08F 214/262; C08F 6/06; C08F 6/12; C02F 1/44; B01D 61/145; B01D 61/243; B01D 61/147; C08L 27/12
See application file for complete search history.

(56) References Cited

U.S. PATENT DOCUMENTS

| | | |
|---|---|---|
| 2003/0023015 A1 | 1/2003 | Tatemoto et al. |
| 2007/0196763 A1 | 8/2007 | Araki et al. |
| 2008/0227948 A1* | 9/2008 | Tsuda ............ C08F 14/18 |
| | | 528/401 |
| 2010/0160598 A1 | 6/2010 | Saito et al. |
| 2018/0186913 A1 | 7/2018 | Watabe et al. |
| 2019/0375866 A1* | 12/2019 | Yotsumoto ........ C08J 3/16 |
| 2022/0195080 A1 | 6/2022 | Higashi et al. |
| 2022/0282007 A1* | 9/2022 | Yamanaka ........ C08F 214/262 |

FOREIGN PATENT DOCUMENTS

| | | | | |
|---|---|---|---|---|
| CN | 1882882 A | | 12/2006 | |
| CN | 1942491 A | | 4/2007 | |
| JP | 2001226436 A | * | 8/2001 | ....... C08F 6/003 |
| JP | 2004-075979 A | | 3/2004 | |
| JP | 2009-122700 A | | 6/2009 | |
| JP | 7295456 B2 | | 6/2023 | |
| WO | 2017/038827 A1 | | 3/2017 | |
| WO | WO-2018070420 A1 | * | 4/2018 | ....... C08F 2/001 |

OTHER PUBLICATIONS

Machine translation into English of JP-2001226436-A; Masanaga (Year: 2001).*
International Preliminary Report on Patentability dated Sep. 28, 2021 with a Translation of the Written Opinion of the International Searching Authority in corresponding Application No. PCT/JP2020/018041.
International Search Report for PCT/JP2020/018041, dated Jul. 28, 2020.
Extended European Search Report dated Dec. 22, 2022 from the European Patent Office in corresponding EP Application No. 20795888.5.

* cited by examiner

*Primary Examiner* — Karuna P Reddy
(74) *Attorney, Agent, or Firm* — Sughrue Mion, PLLC

(57) ABSTRACT

A method for producing a composition including a step A of performing ultrafiltration, microfiltration, dialysis membrane treatment, or a combination thereof on a composition containing water and a fluoropolymer. The fluoropolymer is a polymer having a structural unit M3 derived from a monomer represented by general formula (1):

$$CX_2=CY(-CZ_2-O-Rf-A) \qquad (1)$$

where X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO$_3$M, —OSO$_3$M, or —C(CF$_3$)$_2$OM, wherein M is as defined herein; provided that at least one of X, Y, and Z includes a fluorine atom.

15 Claims, No Drawings

COMPOSITION PRODUCTION METHOD, AND COMPOSITION

CROSS REFERENCE TO RELATED APPLICATIONS

This application is a National Stage of International Application No. PCT/JP2020/018041 filed Apr. 27, 2020, claiming priority based on Japanese Patent Application No. 2019-085980 filed Apr. 26, 2019, Japanese Patent Application No. 2019-184441 filed Oct. 7, 2019, and Japanese Patent Application No. 2019-209162 filed Nov. 19, 2019.

TECHNICAL FIELD

The present disclosure relates to a method for producing a composition and to a composition.

BACKGROUND ART

Recently, fluoropolymers having a sulfonic acid group or a carboxyl group attract attention as materials for electrolyte films and the like of fuel cells, chemical sensors, etc., and research has been conducted.

For example, Patent Document 1 discloses a method for producing a fluorine-containing polymer dispersion, the method comprising the acid treatment step of adding an acid to an aqueous dispersion containing a fluorine-containing polymer precursor to perform ultrafiltration, wherein the fluorine-containing polymer precursor has $-SO_3X^1$ and/or $-COOZ^1$ ($X^1$ represents $M^1_{1/L}$ or $NR^1R^2R^3R^4$; $R^1$, $R^2$, $R^3$, and $R^4$ are the same or different and represent a hydrogen atom or an alkyl group having 1 to 4 carbon atoms; $Z^1$ represents $M^2_{1/L}$ or $NR^5R^6R^7R^8$; $R^5$, $R^6$, $R^7$, and $R^8$ are the same or different and represent a hydrogen atom or an alkyl group having 1 to 4 carbon atoms; $M^1$ and $M^2$ are the same or different and represent an L-valent metal; and the L-valent metal is a metal belonging to Group 1, Group 2, Group 4, Group 8, Group 11, Group 12, or Group 13 of the periodic table), and the acid treatment step is for converting $-SO_3X^1$ to $-SO_3H$ and/or converting $-COOZ^1$ to $-COOH$.

Patent Document 2 discloses a coating composition for forming a photoresist upper layer antireflection film, the composition containing a fluorine-containing polymer having carboxyl group (A1) that is represented by formula (M-3):

-(M3)-(N3)-  (M-3)

[wherein a structural unit M3 is a structural unit derived from a monomer represented by formula (5-1):

wherein $Rf^{10}$ is a divalent fluorine-containing alkylene group having 1 to 40 carbon atoms or a divalent fluorine-containing alkylene group having 2 to 100 carbon atoms and having an ether bond; and a structural unit N3 is a structural unit derived from a monomer copolymerizable with the fluorine-containing monomer of formula (5-1)], that contains the structural unit M3 in an amount of 55 to 100 mol % and the structural unit N3 in an amount of 0 to 45 mol %, and that has a number average molecular weight of $3.1×10^4$ to $75.0×10^4$.

RELATED ART

Patent Documents

Patent Document 1: Japanese Patent Laid-Open No. 2004-75979
Patent Document 2: Japanese Patent Laid-Open No. 2009-122700

SUMMARY OF THE INVENTION

Problem to be Solved by the Invention

The present disclosure provides a method for producing a composition, the method capable of efficiently removing a low molecular weight substance. Also, a composition in which the amount of low molecular weight substance is reduced is provided.

Means for Solving the Problem

The present disclosure is a method for producing a composition, the method comprising a step A of performing ultrafiltration, microfiltration, dialysis membrane treatment, or a combination thereof on a composition comprising water and a fluoropolymer, wherein the fluoropolymer is a polymer comprising a structural unit M3 derived from a monomer represented by general formula (1):

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO_3M, —OSO_3M, or —C(CF_3)_2OM, wherein M is —H, a metal atom, —NR^7_4, imidazolium optionally having a substituent, pyridinium optionally having a substituent, or phosphonium optionally having a substituent, and $R^7$ is H or an organic group; provided that at least one of X, Y, and Z contains a fluorine atom.

In general formula (1), at least one X is preferably —H.
In general formula (1), X is both preferably —H.
In general formula (1), Rf is preferably a fluorine-containing alkylene group having 1 to 10 carbon atoms or a fluorine-containing alkylene group having 2 to 12 carbon atoms and having an ether bond.

The structural unit M3 is preferably a structural unit (1A) based on a monomer represented by the following general formula (1A):

wherein Rf and A are as described above.
The structural unit M3 is preferably a structural unit (1a) based on a fluoroallyl ether compound represented by the following general formula (1a):

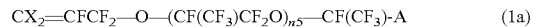

wherein each X is the same and represents F or H; n5 represents 0 or an integer of 1 to 10; and A is as defined above.

A is preferably —COOM.
M is preferably —H, —Na, —K, —Li, or —NH_4.
The fluoropolyrer is preferably a polymer in which the structural unit M3 is 5 to 100 mol % based on all polymerization units, and a structural unit N3 derived from a monomer copolymerizable with the monomer represented by the general formula (1) is 0 to 95 mol % based on all polymerization units.

The structural unit N3 is preferably a structural unit derived from tetrafluoroethylene.

The fluoropolyrer is preferably a polymer having a number average molecular weight of $0.5 \times 10^4$ to $75.0 \times 10^4$.

The fluoropolymer is preferably a polymer in which a proportion of carbon atom-bonded hydrogen atoms replaced with fluorine atoms is 50% or more, which comprises an ionic group, and which has an ion exchange rate of 53 or less.

The fluoropolyrer is preferably a water-soluble polymer in which a proportion of carbon atom-bonded hydrogen atoms replaced with fluorine atoms is 50% or more.

The present disclosure is also a method for producing a composition, the method comprising a step A1 of performing ultrafiltration, microfiltration, dialysis membrane treatment, or a combination thereof on a composition comprising water and a polymer in which a proportion of carbon atom-bonded hydrogen atoms replaced with fluorine atoms is 50% or more, which comprises an ionic group, and which has an ion-exchange rate of 53 or less.

The polymer is preferably a polymer having a number average molecular weight of $0.5 \times 10^4$ to $75.0 \times 10^4$.

The polymer is preferably a water-soluble polymer.

The present disclosure is also a method for producing a composition, the method comprising a step A2 of performing ultrafiltration, microfiltration, dialysis membrane treatment, or a combination thereof on a composition comprising water and a water-soluble polymer in which a proportion of carbon atom-bonded hydrogen atoms replaced with fluorine atoms is 50% or more.

The ultrafiltration, the microfiltration, or the dialysis membrane treatment is preferably performed at a temperature of 20° C. or higher.

The ultrafiltration is preferably performed using an ultrafiltration membrane having a molecular weight cut-off of $1.5 \times 10^4$ Da or more.

The present disclosure is also a composition comprising water and a fluoropolyrer that is a polymer comprising a structural unit M3 derived from a monomer represented by general formula (1):

$$CX_2=CY(-CZ_2-O-Rf-A) \quad (1)$$

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO₃M, —OSO₃M, or —C(CF₃)₂OM, wherein M is —H, a metal atom, —NR⁷₄, imidazolium optionally having a substituent, pyridinium optionally having a substituent, or phosphonium optionally having a substituent, and R⁷ is H or an organic group; provided that at least one of X, Y, and Z contains a fluorine atom,
wherein a content of a compound having a molecular weight of 700 or more and 3,000 or less is 3.5% or less based on the fluoropolymer.

The content of a compound having a molecular weight of 400 or more and 3,000 or less is preferably 3.7% or less based on the fluoropolymer.

The content of a compound having a molecular weight of 700 or more and less than 10,000 is preferably 5.0% or less based on the fluoropolymer.

In general formula (1), at least one X is preferably —H.

In general formula (1), X is both preferably —H.

In general formula (1), Rf is preferably a fluorine-containing alkylene group having 1 to 10 carbon atoms or a fluorine-containing alkylene group having 2 to 12 carbon atoms and having an ether bond.

The structural unit M3 is preferably a structural unit (1A) based on a monomer represented by the following general formula (1A):

$$CH_2=CF(-CF_2-O-Rf-A) \quad (1A)$$

wherein Rf and A are as described above.

The structural unit M3 is preferably a structural unit (1a) based on a fluoroallyl ether compound represented by the following general formula (1a):

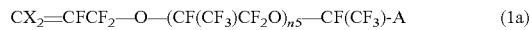

$$CX_2=CFCF_2-O-(CF(CF_3)CF_2O)_{n5}-CF(CF_3)-A \quad (1a)$$

wherein each X is the same and represents F or H; n5 represents 0 or an integer of 1 to 10; and A is as defined above.

A is preferably —COOM.

M is preferably —H, —Na, —K, —Li, or —NH₄.

The fluoropolyrer is preferably a polymer in which the structural unit M3 is 5 to 100 mol % based on all polymerization units, and a structural unit N3 derived from a monomer copolymerizable with the monomer represented by the general formula (1) is 0 to 95 mol % based on all polymerization units.

The fluoropolyrer is preferably a polymer having a number average molecular weight of $0.5 \times 10^4$ to $75.0 \times 10^4$.

The fluoropolymer is preferably a polymer in which a proportion of carbon atom-bonded hydrogen atoms replaced with fluorine atoms is 50% or more, which comprises an ionic group, and which has an ion exchange rate of 53 or less.

The fluoropolyrer is preferably a water-soluble polymer in which a proportion of carbon atom-bonded hydrogen atoms replaced with fluorine atoms is 50% or more.

The present disclosure is also a composition comprising water and a polymer in which a proportion of carbon atom-bonded hydrogen atoms replaced with fluorine atoms is 50% or more, which comprises an ionic group, and which has an ion-exchange rate of 53 or less,
wherein a content of a compound having a molecular weight of 700 or more and 3,000 or less is 3.5% or less based on the polymer.

The content of a compound having a molecular weight of 400 or more and 3,000 or less is preferably 3.7% or less based on the polymer.

The content of a compound having a molecular weight of 700 or more and less than 10,000 is preferably 5.0% or less based on the polymer.

The polymer is preferably a polymer having a number average molecular weight of $0.5 \times 10^4$ to $75.0 \times 10^4$.

The polymer is preferably a water-soluble polymer.

The present disclosure is also a composition comprising water and a water-soluble polymer in which a proportion of carbon atom-bonded hydrogen atoms replaced with fluorine atoms is 50% or more, wherein a content of a compound having a molecular weight of 700 or more and 3,000 or less is 3.5% or less based on the water-soluble polymer.

The content of a compound having a molecular weight of 400 or more and 3,000 or less is preferably 3.7% or less based on the water-soluble polymer.

The content of a compound having a molecular weight of 700 or more and less than 10,000 is preferably 5.0% or less based on the water-soluble polymer.

The present disclosure is also a composition comprising water and a fluoropolymer that is a polymer comprising a structural unit M3 derived from a monomer represented by general formula (1):

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO$_3$M, —OSO$_3$M, or —C(CF$_3$)$_2$OM, wherein M is —H, a metal atom, —NR$^7_4$, imidazolium optionally having a substituent, pyridinium optionally having a substituent, or phosphonium optionally having a substituent, and R$^7$ is H or an organic group; provided that at least one of X, Y, and Z contains a fluorine atom, wherein a content of a dimer and a trimer of a monomer forming a structural unit constituting the fluoropolymer is 2.0% or less based on the fluoropolymer.

The fluoropolymer is preferably a polymer in which a proportion of carbon atom-bonded hydrogen atoms replaced with fluorine atoms is 50% or more, which comprises an ionic group, and which has an ion exchange rate of 53 or less.

The fluoropolymer is preferably a water-soluble polymer in which a proportion of carbon atom-bonded hydrogen atoms replaced with fluorine atoms is 50% or more.

The present disclosure is also a composition comprising water and a polymer in which a proportion of carbon atom-bonded hydrogen atoms replaced with fluorine atoms is 50% or more, which comprises an ionic group, and which has an ion-exchange rate of 53 or less, wherein a content of a dimer and a trimer of a monomer forming a structural unit constituting the polymer is 2.0% or less based on the polymer.

The polymer is preferably a water-soluble polymer.

The present disclosure is also a composition comprising water and a water-soluble polymer in which a proportion of carbon atom-bonded hydrogen atoms replaced with fluorine atoms is 50% or more,
wherein a content of a dimer and a trimer of a monomer forming a structural unit constituting the water-soluble polymer is 2.0% or less based on the water-soluble polymer.

The composition of the present disclosure is preferably a coating agent.

Effects of Invention

The production method of the present disclosure is capable of efficiently removing a low molecular weight substance in a composition.

DESCRIPTION OF EMBODIMENTS

Hereinafter, specific embodiments of the present disclosure will be described in detail, but the present disclosure is not limited to the following embodiments.

The production method of the present disclosure is a method for producing a composition, the method comprising a step A of performing ultrafiltration, microfiltration, dialysis membrane treatment, or a combination thereof on a composition containing water and a fluoropolymer, wherein the fluoropolymer is a polymer containing a structural unit M3 derived from a monomer represented by general formula (1):

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO$_3$M, —OSO$_3$M, or —C(CF$_3$)$_2$OM, wherein M is —H, a metal atom, —NR$^7_4$, imidazolium optionally having a substituent, pyridinium optionally having a substituent, or phosphonium optionally having a substituent, and R$^7$ is H or an organic group; provided that at least one of X, Y, and Z contains a fluorine atom (hereinafter also referred to as the "first production method of the present disclosure").

In the method for producing a fluoropolymer, a fluoropolymer composition containing a low molecular weight substance other than the fluoropolymer is obtained. The first production method of the present disclosure was accomplished through finding that ultrafiltration, microfiltration, or dialysis membrane treatment is particularly effective for the composition containing a specific fluoropolymer, and that low molecular weight substances (e.g., a compound having a molecular weight of 700 or more and 3,000 or less, a compound having a molecular weight of 400 or more and 3,000 or less, a compound having a molecular weight of 700 or more and less than 10,000, a dimer and a trimer of a monomer forming the structural unit M3, a dimer and a trimer of a monomer forming a structural unit constituting a polymer α described below, and a dimer and a trimer of a monomer forming a structural unit constituting the water-soluble polymer described below) can be efficiently removed.

The composition obtained by the first production method of the present disclosure may be an aqueous solution.

In the general formula (1), each X is —H or —F. X may be both —F, or at least one thereof may be —H. For example, one thereof may be —F and the other may be —H, or both may be —H.

In the general formula (1), Y is —H, —F, an alkyl group, or a fluorine-containing alkyl group.

The alkyl group is an alkyl group free from fluorine atoms and may have one or more carbon atoms. The alkyl group preferably has 6 or less carbon atoms, more preferably 4 or less carbon atoms, and still more preferably 3 or less carbon atoms.

The fluorine-containing alkyl group is an alkyl group containing at least one fluorine atom, and may have one or more carbon atoms. The fluorine-containing alkyl group preferably has 6 or less carbon atoms, more preferably 4 or less carbon atoms, and still more preferably 3 or less carbon atoms.

Y is preferably —H, —F, or —CF$_3$, and more preferably —F.

In the general formula (1), Z is the same or different and is —H, —F, an alkyl group, or a fluoroalkyl group.

The alkyl group is an alkyl group free from fluorine atoms and may have one or more carbon atoms. The alkyl group preferably has 6 or less carbon atoms, more preferably 4 or less carbon atoms, and still more preferably 3 or less carbon atoms.

The fluorine-containing alkyl group is an alkyl group containing at least one fluorine atom, and may have one or more carbon atoms. The fluorine-containing alkyl group preferably has 6 or less carbon atoms, more preferably 4 or less carbon atoms, and still more preferably 3 or less carbon atoms.

Z is preferably —H, —F, or —$CF_3$, and more preferably —F.

In the general formula (1), at least one of X, Y, and Z contains a fluorine atom. For example, X may be —H, and Y and Z may be —F.

In the general formula (1), Rf is a fluorine-containing alkylene group having 1 to 40 carbon atoms or a fluorine-containing alkylene group having 2 to 100 carbon atoms and having an ether bond. The fluorine-containing alkylene group having 2 to 100 carbon atoms and having an ether bond is an alkylene group which does not include a structure wherein an oxygen atom is an end and which contains an ether bond between carbon atoms.

The fluorine-containing alkylene group preferably has 2 or more carbon atoms. Further, the fluorine-containing alkylene group preferably has 30 or less carbon atoms, more preferably 20 or less carbon atoms, and still more preferably 10 or less carbon atoms. Examples of the fluorine-containing alkylene group include —$CF_2$—, —$CH_2CF_2$—, —$CF_2CF_2$—, —$CF_2CH_2$—, —$CF_2CF_2CH_2$—, —$CF(CF_3)$—, —$CF(CF_3)CF_2$—, and —$CF(CF_3)CH_2$—. The fluorine-containing alkylene group is preferably a perfluoroalkylene group.

The fluorine-containing alkylene group having an ether bond preferably has 3 or more carbon atoms. Further, the fluorine-containing alkylene group having an ether bond preferably has 60 or less, more preferably 30 or less, and still more preferably 12 or less carbon atoms.

The fluorine-containing alkylene group having an ether bond is also preferably a divalent group represented by the following formula:

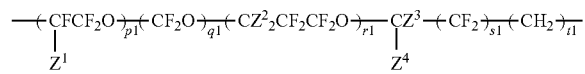

(wherein $Z^1$ is F or $CF_3$; $Z^2$ and $Z^3$ are each H or F; $Z^4$ is H, F, or $CF_3$; p1+q1+r1 is an integer of 1 to 10; s1 is 0 or 1; and t1 is an integer of 0 to 5).

Specific examples of the fluorine-containing alkylene group having an ether bond include —$CF(CF_3)CF_2$—O—$CF(CF_3)$—, —$(CF(CF_3)CF_2$—O$)_n$—$CF(CF_3)$— (wherein n is an integer of 1 to 10), —$CF(CF_3)CF_2$—O—$CF(CF_3)$$CH_2$—, —$(CF(CF_3)CF_2$—O$)_n$—$CF(CF_3)CH_2$— (wherein n is an integer of 1 to 10), —$CH_2CF_2CF_2$O—$CH_2CF_2CH_2$—, —$CF_2CF_2CF_2$O—$CF_2CF_2$—, —$CF_2CF_2CF_2$O—$CF_2CF_2CH_2$—, —$CF_2CF_2$O—$CF_2$—, and —$CF_2CF_2$O—$CF_2CH_2$—. The fluorine-containing alkylene group having an ether bond is preferably a perfluoroalkylene group.

In the general formula (1), A is —COOM, —$SO_3$M, —$OSO_3$M, or —$C(CF_3)_2$OM, wherein M is —H, a metal atom, —$NR^7_4$, imidazolium optionally having a substituent, pyridinium optionally having a substituent, or phosphonium optionally having a substituent, and $R^7$ is H or an organic group.

$R^7$ is preferably H or a $C_{1-10}$ organic group, more preferably H or a $C_{1-4}$ organic group, and still more preferably H or a $C_{1-4}$ alkyl group.

Examples of the metal atom include alkali metals (Group 1) and alkaline earth metals (Group 2), and preferred is Na, K, or Li.

M is preferably —H, a metal atom, or —$NR^7_4$, more preferably —H, an alkali metal (Group 1), an alkaline earth metal (Group 2), or —$NR^7_4$, still more preferably —H, —Na, —K, —Li, or —$NH_4$, further preferably —Na, —K, or —$NH_4$, particularly preferably —Na or —$NH_4$, and most preferably —$NH_4$.

A is preferably —COOM or —$SO_3$M, and more preferably —COOM.

The structural unit M3 is suitably a structural unit (1a) based on a fluoroallyl ether compound represented by the following formula (1a):

$$CX_2=CFCF_2—O—(CF(CF_3)CF_2O)_{n5}—CF(CF_3)\text{-}A \quad (1a)$$

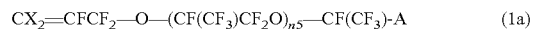

wherein each X is the same and represents F or H; n5 represents 0 or an integer of 1 to 10; and A is as defined above.

In the general formula (1a), n5 is preferably 0 or an integer of 1 to 5, more preferably 0, 1, or 2, and still more preferably 0 or 1 from the viewpoint of obtaining fluoropolymer particles having a small primary particle size. A is preferably —COOM from the viewpoint of obtaining appropriate water-solubility and surface activity, and M is preferably H or $NH_4$ from the viewpoint of being less likely to remain as impurities and improving the heat resistance of the resulting composition.

The structural unit M3 is preferably a structural unit (1A) based on a monomer represented by the following general formula (1A):

$$CH_2=CF(—CF_2—O—Rf\text{-}A) \quad (1A)$$

wherein Rf and A are as described above.

Specific examples of the monomer represented by the general formula (1A) include a monomer represented by the following formula:

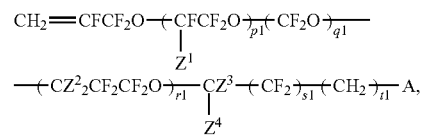

wherein $Z^1$ is F or $CF_3$; $Z^2$ and $Z^3$ are each H or F; $Z^4$ is H, F, or $CF_3$; p1+q1+r1 is an integer of 0 to 10; s1 is 0 or 1; t1 is an integer of 0 to 5, with the proviso that when $Z^3$ and $Z^4$ are both H, p1+q1+r1+s1 is not 0; and A is as defined above. More specifically, preferred examples thereof include:

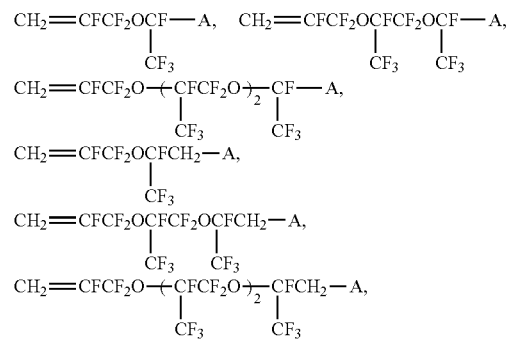

$CH_2$=$CFCF_2OCH_2CF_2$-A, $CH_2$=$CFCF_2O(CH_2CF_2CF_2O)$ $CH_2CF_2$-A, $CH_2$=$CFCF_2OCH_2CF_2CH_2$-A, $CH_2$=$CFCF_2O(CH_2CF_2CF_2O)CH_2CF_2CH_2$-A, $CH_2$=$CFCF_2OCF_2CF_2$-A, $CH_2$=$CFCF_2O(CF_2CF_2CF_2O)$ $CF_2CF_2$-A, $CH_2$=$CFCF_2OCF_2CF_2CH_2$-A, $CH_2$=$CFCF_2O$ $(CF_2CF_2CF_2O)CF_2CF_2CH_2$-A, $CH_2$=$CFCF_2OCF_2$-A, $CH_2$=$CFCF_2O(CF_2CF_2O)CF_2$-A, $CH_2$=$CFCF_2OCF_2CH_2$-A, $CH_2$=$CFCF_2O(CF_2CF_2O)$ $CF_2CH_2$-A,

Of these,

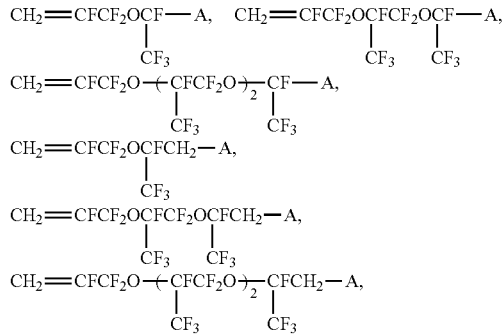

are preferable.

In the monomer represented by the general formula (1A), A in the formula (1A) is preferably —COOM. Specifically, the monomer represented by the general formula (1A) is preferably at least one selected from the group consisting of $CH_2$=$CFCF_2OCF(CF_3)COOM$ and $CH_2$=$CFCF_2OCF$ $(CF_3)CF_2OCF(CF_3)COOM$ (wherein M is as defined above), and more preferably $CH_2$=$CFCF_2OCF(CF_3)$ COOM.

Examples of the monomer represented by the general formula (1) further include monomers represented by the following formulas:

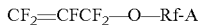

wherein Rf and A are as described above.
More specific examples thereof include:

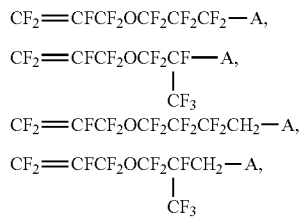

The structural unit M3 is also preferably a structural unit (1') based on a monomer represented by the following general formula (1'):

wherein $Rf^{10}$ is a fluorine-containing alkylene group having 1 to 40 carbon atoms or a fluorine-containing alkylene group having 2 to 100 carbon atoms and having an ether bond.

In the general formula (1'), $Rf^{10}$ is a fluorine-containing alkylene group having 1 to 40 carbon atoms or a fluorine-containing alkylene group having 2 to 100 carbon atoms and having an ether bond. The fluorine-containing alkylene group having 2 to 100 carbon atoms and having an ether bond is an alkylene group which does not include a structure wherein an oxygen atom is an end and which contains an ether bond between carbon atoms.

The fluorine-containing alkylene group preferably has 2 or more carbon atoms. The fluorine-containing alkylene group also preferably has 30 or less carbon atoms, more preferably 20 or less carbon atoms, and still more preferably 10 or less carbon atoms. Examples of the fluorine-containing alkylene group include —$CF_2$—, —$CH_2CF_2$—, —$CF_2CF_2$—, —$CF_2CH_2$—, —$CF_2CF_2CH_2$—, —$CF(CF_3)$—, —$CF(CF_3)CF_2$—, and —$CF(CF_3)CH_2$—. The fluorine-containing alkylene group is preferably a perfluoroalkylene group.

The fluorine-containing alkylene group having an ether bond preferably has 3 or more carbon atoms. Further, the fluorine-containing alkylene group having an ether bond preferably has 60 or less, more preferably 30 or less, and still more preferably 12 or less carbon atoms.

The fluorine-containing alkylene group having an ether bond is also preferably a divalent group represented by the following formula:

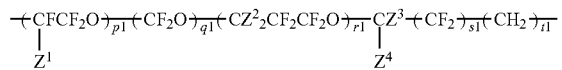

(wherein $Z^1$ is F or $CF_3$; $Z^2$ and $Z^3$ are each H or F; $Z^4$ is H, F, or $CF_3$; p1+q1+r1 is an integer of 1 to 10; s1 is 0 or 1; and t1 is an integer of 0 to 5).

Specific examples of the fluorine-containing alkylene group having an ether bond include —$CF(CF_3)CF_2$—O— $CF(CF_3)$—, —$(CF(CF_3)CF_2$—O$)_n$—$CF(CF_3)$— (wherein n is an integer of 1 to 10), —$CF(CF_3)CF_2$—O—$CF(CF_3)$ $CH_2$—, —$(CF(CF_3)CF_2$—O$)_n$—$CF(CF_3)CH_2$— (wherein n is an integer of 1 to 10), —$CH_2CF_2CF_2O$—$CH_2CF_2CH_2$—, —$CF_2CF_2CF_2O$—$CF_2CF_2$—, —$CF_2CF_2CF_2O$— $CF_2CF_2CH_2$—, —$CF_2CF_2O$—$CF_2$—, and —$CF_2CF_2O$— $CF_2CH_2$—. The fluorine-containing alkylene group having an ether bond is preferably a perfluoroalkylene group.

Specific examples of the monomer represented by the general formula (1') include a monomer represented by the following formula:

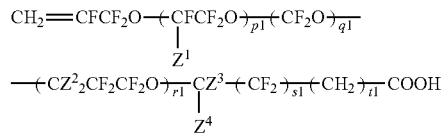

wherein $Z^1$ is F or $CF_3$; $Z^2$ and $Z^3$ are each H or F; $Z^4$ is H, F, or $CF_3$; p1+q1+r1 is an integer of 0 to 10; s1 is 0 or 1; and t1 is an integer of 0 to 5, with the proviso that when $Z^3$ and $Z^4$ are both H, p1+q1+r1+s1 is not 0. More specifically, preferred examples thereof include:

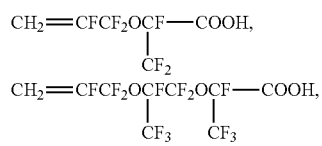

-continued $CH_2=CFCF_2O+CFCF_2O)_{\overline{2}}CF-COOH$,
     |           |
     $CF_3$      $CF_3$ $CH_2=CFCF_2OCFCH_2-COOH$,
         |
         $CF_3$ $CH_2=CFCF_2OCFCF_2OCFCH_2-COOH$,
         |        |
         $CF_3$   $CF_3$ $CH_2=CFCF_2O+CFCF_2O)_{\overline{2}}CFCH_2-COOH$,
     |            |
     $CF_3$       $CF_3$ $CH_2=CFCF_2OCH_2CF_2-COOH$, $CH_2=CFCF_2(CH_2CF_2CF_2O)CH_2CF_2-COOH$,
$CH_2=CFCF_2OCH_2CF_2CH_2-COOH$, $CH_2=CFCF_2(CH_2CF_2CF_2O)CH_2CF_2CH_2-COOH$,
$CH_2=CFCF_2OCF_2CF_2-COOH$, $CH_2=CFCF_2O(CF_2CF_2CF_2O)CF_2CF_2-COOH$,
$CH_2=CFCF_2OCF_2CF_2CH_2-COOH$, $CH_2=CFCF_2O(CF_2CF_2CF_2O)CF_2CF_2CH_2-COOH$,
$CH_2=CFCF_2OCF_2-COOH$, $CH_2=CFCF_2O(CF_2CF_2O)CF_2-COOH$, $CH_2=CFCF_2OCF_2CH_2-COOH$,
$CH_2=CFCF_2O(CF_2CF_2O)CF_2CH_2COOH$, Of these, preferred are:

$CH_2=CFCF_2OCF-COOH$,
         |
         $CF_2$ $CH_2=CFCF_2OCFCF_2OCF-COOH$,
         |        |
         $CF_3$   $CF_3$ $CH_2=CFCF_2O+CFCF_2O)_{\overline{2}}CF-COOH$,
     |            |
     $CF_3$       $CF_3$ $CH_2=CFCF_2OCFCH_2-COOH$,
         |
         $CF_3$ $CH_2=CFCF_2OCFCF_2OCFCH_2-COOH$,
         |        |
         $CF_3$   $CF_3$ $CH_2=CFCF_2O+CFCF_2O)_{\overline{2}}CFCH_2-COOH$,
     |            |
     $CF_3$       $CF_3$ The monomer represented by the general formula (1') in particular is suitably a fluoroallyl ether compound represented by the following formula (1a'):

$CH_2=CFCF_2O-(CF(CF_3)CF_2O)_{n5}-CF(CF_3)-COOH$ (1a')

wherein n5 represents 0 or an integer of 1 to 10.

In the general formula (1a'), n5 is preferably 0 or an integer of 1 to 5, more preferably 0, 1, or 2, and still more preferably 0 or 1.

The monomer represented by the general formula (1a') is, in particular, preferably at least one selected from the group consisting of $CH_2=CFCF_2OCF(CF_3)COOH$ and $CH_2=CFCF_2OCF(CF_3)CF_2OCF(CF_3)COOH$, and more preferably $CH_2=CFCF_2OCF(CF_3)COOH$.

The fluoropolymer may be a homopolymer composed solely of the structural unit M3, or may be a copolymer containing the structural unit M3 and a structural unit N3 derived from a monomer copolymerizable with the monomer represented by the general formula (1). From the viewpoint of solubility in a polymerization medium, a homopolymer composed solely of the structural unit M3 is preferable. The structural unit M3 may be the same or different at each occurrence, and the fluoropolymer may contain the structural unit M3 derived from two or more different monomers represented by the general formula (1).

The monomer copolymerizable with a monomer represented by the general formula (1) is preferably a fluorine-containing ethylenic monomer having 2 or 3 carbon atoms, such as $CF_2=CF_2$, $CF_2=CFCl$, $CH_2=CF_2$, $CFH=CH_2$, $CFH=CF_2$, $CF_2=CFCF_3$, $CH_2=CFCF_3$, $CH_2=CHCF_3$, $CHF=CHCF_3$ (E-form), and $CHF=CHCF_3$ (Z-form).

Among these, from the viewpoint of good copolymerizability, at least one selected from the group consisting of tetrafluoroethylene ($CF_2=CF_2$), chlorotrifluoroethylene ($CF_2=CFCl$), and vinylidene fluoride ($CH_2=CF_2$) is preferable, and tetrafluoroethylene is more preferable. Accordingly, the structural unit N3 is preferably a structural unit derived from tetrafluoroethylene. The structural unit N3 may be the same or different at each occurrence, and the fluoropolymer may contain the structural unit N3 derived from a monomer copolymerizable with two or more different monomers represented by the general formula (1).

Examples of the monomer copolymerizable with a monomer represented by the general formula (1) include a monomer represented by the following formula (n1-2):

$$CX^1X^2=CX^3 \atop |  \atop (CX^4X^5)_a(O)_c-Rf^3 \qquad (n1\text{-}2)$$

wherein $X^1$ and $X^2$ are the same or different and H or F; $X^3$ is H, F, Cl, $CH_3$, or $CF_3$; $X^4$ and $X^5$ are the same or different and H or F; a and c are the same or different and 0 or 1; and $Rf^3$ is a fluorine-containing alkyl group having 1 to 40 carbon atoms or a fluorine-containing alkyl group having 2 to 100 carbon atoms and having an ether bond.

Specifically, preferable examples include $CH_2=CFCF_2-O-Rf^3$, $CF_2=CF-O-Rf^3$, $CF_2=CFCF_2-O-Rf^3$, $CF_2=CF-Rf^3$, $CH_2=CH-Rf^3$, and $CH_2=CH-O-Rf^3$ (wherein $Rf^3$ is as in the above formula (n1-2)).

Examples of the further monomer also include a fluorine-containing acrylate monomer represented by formula (n2-1):

$$CH_2=CX^9 \atop | \atop COO-Rf^4 \qquad (n2\text{-}1)$$

wherein $X^9$ is H, F, or $CH_3$; and $Rf^4$ is a fluorine-containing alkyl group having 1 to 40 carbon atoms or a fluorine-containing alkyl group having 2 to 100 carbon atoms and having an ether bond. Examples of the $Rf^4$ group include:

$$-(CH_2)_{c1}(CF_2)_{c1}-Z^8$$

wherein $Z^8$ is H, F, or Cl; d1 is an integer of 1 to 4; and e1 is an integer of 1 to 10,

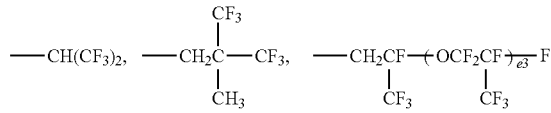

wherein e2 is an integer of 1 to 5,

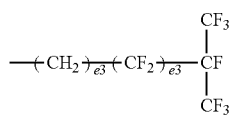

wherein d3 is an integer of 1 to 4; and e3 is an integer of 1 to 10.

Examples of the monomer copolymerizable with a monomer represented by the general formula (1) include formula (n2-2):

$$CH_2\!=\!CHO\!-\!Rf^5 \qquad (n2\text{-}2)$$

wherein $Rf^5$ is a fluorine-containing alkyl group having 1 to 40 carbon atoms or a fluorine-containing alkyl group having 2 to 100 carbon atoms and having an ether bond.

Specifically, preferable examples of the monomer of the formula (n2-2) include:

wherein $Z^9$ is H or F; and e4 is an, integer of 1 to 10,

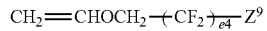

wherein e5 is an integer of 1 to 10,

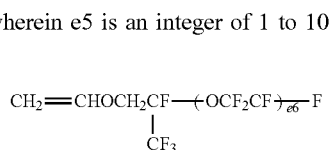

wherein e6 is an integer of 1 to 10.
More specific examples thereof include:

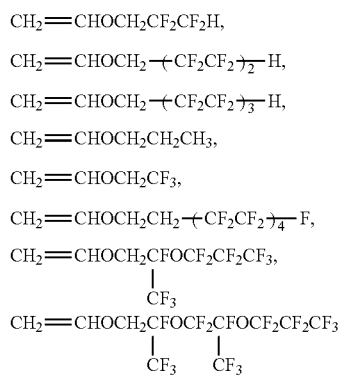

and the like.

In addition, examples also include a fluorine-containing allyl ether represented by the formula (n2-3):

$$CH_2\!=\!CHCH_2O\!-\!Rf^6 \qquad (n2\text{-}3)$$

wherein $Rf^6$ is a fluorine-containing alkyl group having 1 to 40 carbon atoms or a fluorine-containing alkyl group having 2 to 100 carbon atoms and having an ether bond; and a fluorine-containing vinyl ether represented by the formula (n2-4):

$$CH_2\!=\!CH\!-\!Rf^7 \qquad (n2\text{-}4)$$

wherein $Rf^7$ is a fluorine-containing alkyl group having 1 to 40 carbon atoms or a fluorine-containing alkyl group having 2 to 100 carbon atoms and having an ether bond.

Specific examples of monomers represented by formulas (n2-3) and (n2-4) include monomers such as:

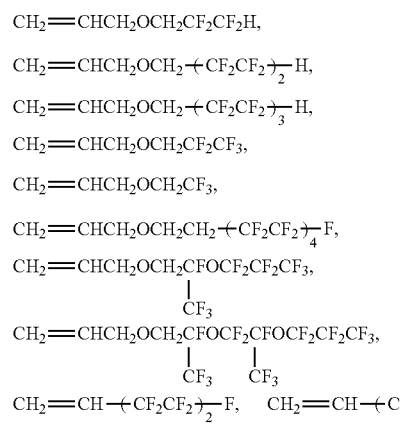

and the like.

The content of the structural unit M3 in the fluoropolymer is preferably 1.0 mol % or more, more preferably 3.0 mol % or more, still more preferably 5.0 mol % or more, further preferably 10 mol % or more, still further preferably 20 mol % or more, and particularly preferably 30 mol % or more based on all polymerization units. The content is more preferably 40 mol % or more, still more preferably 60 mol % or more, further preferably 80 mol % or more, particularly preferably 90 mol % or more, and still further preferably substantially 100 mol %, and the fluoropolymer is most preferably composed solely of the structural unit M3.

The content of the structural unit N3 in the fluoropolymer is preferably 99.0 mol % or less, more preferably 97.0 mol % or less, still more preferably 95.0 mol % or less, further preferably 90 mol % or less, still further preferably 80 mol % or less, and particularly preferably 70 mol % or less based on all polymerization units. The content is more preferably 60 mol % or less, still more preferably 40 mol % or less, further preferably 20 mol % or less, particularly preferably 10 mol % or less, and still further preferably substantially 0 mol %. Particularly still further preferably, the fluoropolymer does not contain the structural unit N3.

It is one particularly preferable embodiment that in the fluoropolymer, the structural unit M3 is a structural unit derived from a fluoroallyl ether compound represented by the following formula (1a):

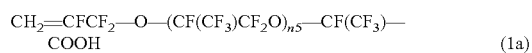

wherein n5 represents 0 or an integer of 1 to 10, and the structural unit N3 is a structural unit derived from tetrafluoroethylene.

In the fluoropolymer, the content of a structural unit derived from a fluoroallyl ether compound represented by the formula (1a) is preferably 10 mol % or more, more preferably 20 mol % or more, still more preferably 30 mol % or more, further preferably 40 mol % or more, still further preferably 60 mol % or more, particularly preferably 80 mol % or more, particularly preferably 90 mol % or more, and particularly preferably substantially 100 mol % based on all polymerization units.

Further, in the fluoropolymer, the content of a structural unit derived from tetrafluoroethylene is preferably 90 mol % or less, more preferably 80 mol % or less, still more preferably 70 mol % or less, further preferably 60 mol % or less, still further preferably 40 mol % or less, particularly preferably 20 mol % or less, particularly preferably 10 mol % or less, and particularly preferably substantially 0 mol % based on all polymerization units.

The number average molecular weight of the fluoropolymer is preferably $0.1 \times 10^4$ or more, more preferably $0.2 \times 10^4$ or more, still more preferably $0.3 \times 10^4$ or more, further preferably $0.4 \times 10^4$ or more, still further preferably $0.5 \times 10^4$ or more, particularly preferably $1.0 \times 10^4$ or more, very particularly preferably $3.0 \times 10^4$ or more, and most preferably $3.1 \times 10^4$ or more. The number average molecular weight is preferably $75.0 \times 10^4$ or less, more preferably $50.0 \times 10^4$ or less, still more preferably $40.0 \times 10^4$ or less, still further preferably $30.0 \times 10^4$ or less, and particularly preferably $20.0 \times 10^4$ or less.

When the number average molecular weight is excessively low, dispersibility (property of stably dispersing other components) is decreased, and possibly the composition cannot be used as a dispersant. When the number average molecular weight is excessively high, viscosity is more increased, and handling may become troublesome.

The weight average molecular weight of the fluoropolymer is preferably $0.2 \times 10^4$ or more, more preferably $0.4 \times 10^4$ or more, still more preferably $0.6 \times 10^4$ or more, further preferably $0.8 \times 10^4$ or more, particularly preferably $1.0 \times 10^4$ or more, more particularly preferably $5.0 \times 10^4$ or more, still particularly preferably $10.0 \times 10^4$ or more, still further preferably $15.0 \times 10^4$ or more, very particularly preferably $20.0 \times 10^4$ or more, and most preferably $25.0 \times 10^4$ or more. The weight average molecular weight is preferably $150.0 \times 10^4$ or less, more preferably $100.0 \times 10^4$ or less, still more preferably $60.0 \times 10^4$ or less, particularly preferably $50.0 \times 10^4$ or less, and further preferably $40.0 \times 10^4$ or less.

The number average molecular weight and the weight average molecular weight are molecular weight values calculated by gel permeation chromatography (GPC) using monodisperse polyethylene oxide (PEO) and polyethylene glycol (PEG) manufactured by Tosoh Corporation and Agilent as standards. Further, when measurement by GPC is not possible, the number average molecular weight of the fluoropolymer can be determined by the correlation between the number average molecular weight calculated from the number of terminal groups obtained by NMR, FT-IR, or the like, and the melt flow rate. The melt flow rate can be measured in accordance with JIS K 7210.

In the fluoropolymer, the proportion of carbon atom-bonded hydrogen atoms replaced with fluorine atoms is preferably 50% or more. The "proportion of carbon atom-bonded hydrogen atoms replaced with fluorine atoms" is obtained as the proportion of the number of fluorine atoms to the total number of hydrogen atoms bonded to carbon atoms and halogen atoms (including fluorine atoms) bonded to carbon atoms. The proportion of carbon atom-bonded hydrogen atoms replaced with fluorine atoms in the fluoropolymer is not limited, and is more preferably 80% or more, still more preferably 90% or more, particularly preferably 95% or more, and most preferably 100%.

The fluoropolyrer preferably contains an ionic group.

The fluoropolyrer preferably has an ion exchange rate (IXR) of 53 or less. The IXR is defined as the number of carbon atoms in the polymer backbone relative to the ionic group. A precursor group that becomes ionic by hydrolysis (such as $-SO_2F$) is not regarded as an ionic group for the purpose of determining the IXR.

The IXR is preferably 0.5 or more, more preferably 1 or more, still more preferably 3 or more, further preferably 4 or more, still further preferably 5 or more, and particularly preferably 8 or more. The IXR is preferably 43 or less, more preferably 33 or less, and still more preferably 23 or less.

In the fluoropolymer, the ionic groups are typically distributed along the polymer backbone. The fluoropolyrer contains the polymer backbone together with a repeating side chain bonded to this backbone, and this side chain preferably has an ionic group.

The fluoropolyrer preferably contains an ionic group having a pKa of less than 10, and more preferably less than 7. The ionic group of the fluoropolymer is preferably selected from the group consisting of sulfonate, carboxylate, phosphonate, and phosphate.

The terms "sulfonate, carboxylate, phosphonate, and phosphate" are intended to refer to the respective salts or the respective acids that can form salts. A salt when used is preferably an alkali metal salt or an ammonium salt. A preferable ionic group is a sulfonate group.

The fluoropolyrer is preferably a water-soluble polymer. "Water-solubility" means the property of being readily dissolved or dispersed in an aqueous medium. The particle size of a water-soluble polymer cannot be measured by, for example, dynamic light scattering (DLS). On the other hand, the particle size of a non-water-soluble polymer can be measured by, for example, dynamic light scattering (DLS).

The fluoropolymer can be produced by a conventionally known method except that the above-described monomer is used.

In the composition containing water and the fluoropolyrer, the concentration of the fluoropolymer is not limited and may be, for example, 0.1 to 20% by mass.

The concentration of the fluoropolymer in the composition is preferably 18.0% by mass or less because the efficiency of removing a low molecular weight substance is more increased. The concentration is more preferably 15.0% by mass or less, still more preferably 12.0% by mass or less, and particularly preferably 10.0% by mass or less. By adjusting the concentration of the fluoropolymer within the above range, a low molecular weight substance can be more efficiently removed. The concentration of the fluoropolymer is preferably 0.5% by mass or more, more preferably 1.0% by mass or more, still more preferably 1.2% by mass or more, and particularly preferably 1.5% by mass or more.

The composition containing water and the fluoropolymer may solely contain one fluoropolymer, or may contain two or more different fluoropolymers.

The composition containing water and the fluoropolymer preferably has a pH of 0 to 11, and more preferably 0.5 to 8.0. The pH can be adjusted by using a pH adjuster. The pH adjuster may be an acid or an alkali, such as a phosphoric acid salt, sodium hydroxide, potassium hydroxide, or aqueous ammonia.

It is also preferable that the first production method of the present disclosure comprises the step of adjusting the pH of the composition containing water and the fluoropolymer to 1.0 to 7.0 before the step A.

The composition containing water and the fluoropolymer may be obtained by, for example, polymerizing a monomer represented by the general formula (1). It is also one preferable embodiment that the first production method of the present disclosure comprises the step of polymerizing a monomer represented by the general formula (1) (hereinafter also referred to as a "polymerization step"). The polymerization step is preferably performed in an aqueous medium. That is to say, the first production method of the present disclosure also preferably comprises the step of polymerizing a monomer represented by the general formula (1) in an aqueous medium to obtain a composition containing water and a fluoropolymer.

The polymerization step is not limited as long as a composition containing water and a fluoropolymer is obtained, and a known method can be employed.

The composition containing water and the fluoropolymer may be a composition directly obtained from polymerization, may be what is obtained after diluting or concentrating a composition directly obtained from polymerization, or may be what is obtained after performing dispersion stabilization treatment or the like. In order to facilitate ultrafiltration, microfiltration, or dialysis membrane treatment, it is also preferable to adjust the viscosity of the composition containing the fluoropolymer by these treatments.

The viscosity of the composition containing water and a fluoropolyrer used in the step A is preferably 25 mPa·s or less because ultrafiltration, microfiltration, or dialysis membrane treatment is facilitated. The viscosity of the composition can be adjusted by, for example, a method involving adjusting the number average molecular weight of the fluoropolymer, a method involving adjusting the concentration of the fluoropolymer in the composition, or a method involving adjusting the temperature of the composition.

Due to the polymerization, a low molecular weight substance is usually produced as a by-product. In the first production method of the present disclosure, the low molecular weight substance can be removed by performing a treatment such as ultrafiltration on the composition containing water and a fluoropolymer.

The composition containing water and the fluoropolymer used in the step A may contain a low molecular weight substance, and, for example, the content of the low molecular weight substance is preferably more than 5.0%, more preferably 5.5% or more, still more preferably 6.0% or more, or more than 2.0% based on the fluoropolymer.

Examples of the low molecular weight substance include a compound having a molecular weight of 700 or more and 3,000 or less, a compound having a molecular weight of 400 or more and 3,000 or less, a compound having a molecular weight of 700 or more and less than 10,000, a dimer and a trimer of a monomer forming the structural unit M3, a dimer and a trimer of a monomer forming a structural unit constituting the polymer α described below, and a dimer and a trimer of a monomer forming a structural unit constituting the water-soluble polymer described below.

The content of the low molecular weight substance is a value calculated from the peak area of GPC and/or a value calculated by liquid chromatography-mass spectrometry (LC/MS/MS) measurement.

The ultrafiltration or microfiltration is not limited and may be performed by a cross-flow method or a dead-end method, but a cross-flow method is preferable from the viewpoint of reducing the clogging of a membrane.

The ultrafiltration can be performed using an ultrafiltration membrane. Ultrafiltration can be performed using, for example, an ultrafiltration apparatus having an ultrafiltration membrane, and a centrifugal ultrafiltration method, a batch-type ultrafiltration method, a circulation-type ultrafiltration method, and the like can be employed.

The molecular weight cut-off of the ultrafiltration membrane is usually about $0.1 \times 10^4$ to $30 \times 10^4$ Da. The lower limit of the molecular weight cut-off of the ultrafiltration membrane is, in order of preference, $0.3 \times 10^4$ Da or more, $0.5 \times 10^4$ Da or more, $1.0 \times 10^4$ Da or more, $1.5 \times 10^4$ Da or more, $2.0 \times 10^4$ Da or more, $3.0 \times 10^4$ Da or more, $5.0 \times 10^4$ Da or more, or $8.0 \times 10^4$ Da or more because the clogging of the membrane can be suppressed, and the amount of low molecular weight substance can be efficiently reduced.

Further, from the viewpoint of reducing the amount of low molecular weight substance, the molecular weight cut-off is preferably $20 \times 10^4$ Da or less, and more preferably $10 \times 10^4$ Da or less.

The molecular weight cut-off of the ultrafiltration membrane can be, for example, a molecular weight at which 90% of polystyrene having a known weight average molecular weight that is attempted to pass through the membrane is blocked. The quantification of polystyrene can be performed using gel permeation chromatography.

In particular, in order to efficiently remove a compound having a molecular weight of 700 or more and 3,000 or less, a compound having a molecular weight of 400 or more and 3,000 or less, a compound having a molecular weight of 700 or more and less than 10,000, and the like from the composition containing the fluoropolymer, ultrafiltration is preferably performed on the composition containing the fluoropolymer. The molecular weight cut-off of the ultrafiltration membrane used at this time is preferably $1.0 \times 10^4$ Da or more and more preferably $1.5 \times 10^4$ Da or more, and is preferably $20.0 \times 10^4$ Da or less and more preferably $10.0 \times 10^4$ Da or less.

The ultrafiltration membrane is not limited and may be in a conventionally known form, and examples include a hollow fiber type, a flat membrane type, a spiral type, and a tubular type. From the viewpoint of suppressing clogging, a hollow fiber type is preferable.

The inner diameter of the hollow fiber type ultrafiltration membrane is not limited, and may be, for example, 0.1 to 2 mm, and is preferably 0.8 to 1.4 mm.

The length of the hollow fiber type ultrafiltration membrane is not limited, and may be, for example, 0.05 to 3 m, and is preferably 0.05 to 2 m.

The material of the ultrafiltration membrane is not limited, and examples include organic materials such as cellulose, cellulose ester, polysulfone, sulfonated polysulfone, polyethersulfone, sulfonated polyether sulfone, chlorinated polyethylene, polypropylene, polyolefin, polyvinyl alcohol, polymethylmethacrylate, polyacrylonitrile, polyvinylidene fluoride, and polytetrafluoroethylene, metals such as stainless steel, and inorganic materials such as ceramics.

The material of the ultrafiltration membrane is preferably an organic material, more preferably chlorinated polyethylene, polypropylene, polyvinylidene fluoride, polytetrafluoroethylene, polyacrylonitrile, polysulfone, or polyethersulfone, and still more preferably polyacrylonitrile or polyvinylidene fluoride.

Specific examples of the ultrafiltration membrane include G-5 type, G-10 type, G-20 type, G-50 type, PW type, and HWS UF type of DESAL; HFM-180, HFM-183, HFM-251, HFM-300, HFM-116, HFM-183, HFM-300, HFK-131, HFK-328, MPT-U20, MPS-U20P, and MPS-U20S of KOCH; SPE1, SPE3, SPES, SPE10, SPE30, SPV5, SPV50, and SOW30 of Synder; Microza® UF series manufactured by Asahi Kasei Corporation; and NTR 7410 manufactured by Nitto Denko Corporation.

From the viewpoint of reducing the amount of low molecular weight substance, the ultrafiltration is preferably performed at a pressure of 0.01 MPa or more. More preferably, the pressure is 0.03 MPa or more, and still more preferably 0.05 MPa or more. Further, from the viewpoint of pressure resistance, the pressure is preferably 0.5 MPa or less, more preferably 0.25 MPa or less, and still more preferably 0.2 MPa or less.

From the viewpoint of reducing the amount of low molecular weight substance, the ultrafiltration is preferably performed at a flow rate of 10 mL/min or more and more preferably performed at a flow rate of 50 mL/min or more, and is preferably performed at a flow rate of 5,000 mL/min or less and more preferably performed at a flow rate of 1,000 mL/min or less.

The microfiltration can be performed using a microfiltration membrane. The microfiltration membrane usually has an average pore size of 0.05 to 1.0 μm.

The microfiltration membrane preferably has an average pore size of 0.1 μm or more because the amount of low molecular weight substance can be efficiently reduced. The average pore size is more preferably 0.075 μm or more, and still more preferably 0.1 μm or more. Further, the average pore size is preferably 1.00 μm or less. The average pore size is more preferably 0.50 μm or less, and still more preferably 0.25 μm or less.

The average pore size of the microfiltration membrane can be measured in accordance with ASTM F316 03 (bubble point method).

The microfiltration membrane is not limited and may be in a conventionally known form, and examples include a hollow fiber type, a flat membrane type, a spiral type, and a tubular type. From the viewpoint of suppressing clogging, a hollow fiber type is preferable.

The inner diameter of the hollow fiber type ultrafiltration membrane is not limited, and may be, for example, 0.1 to 2 mm, and is preferably 0.8 to 1.4 mm.

The length of the hollow fiber type ultrafiltration membrane is not limited, and may be, for example, 0.05 to 3 m, and is preferably 0.05 to 2 m.

Examples of the material of the microfiltration membrane include cellulose, aromatic polyamide, polyvinyl alcohol, polysulfone, polyether sulfone, polyvinylidene fluoride, polyethylene, polyacrylonitrile, polypropylene, polycarbonate, polytetrafluoroethylene, ceramics, and metal. Among these, aromatic polyamide, polyvinyl alcohol, polysulfone, polyvinylidene fluoride, polyethylene, polyacrylonitrile, polypropylene, polycarbonate, or polytetrafluoroethylene is preferable, and polyacrylonitrile or polyvinylidene fluoride is particularly preferable.

Specific examples of the microfiltration membrane include Cefilt manufactured by NGK Insulators, Ltd.; Microza U Series and Microza P Series manufactured by Asahi Kasei Corporation; Poreflon SPMW, Poreflon OPMW, and Poreflon PM manufactured by Sumitomo Electric Industries, Ltd.; Trayfil manufactured by Toray Industries, Inc.; NADIR MP005 and NADIR MV020 manufactured by Microdyn-Nadir; and X-Flow manufactured by Norit.

From the viewpoint of reducing the amount of low molecular weight substance, the microfiltration is preferably performed at a pressure of 0.01 MPa or more. The pressure is more preferably 0.03 MPa or more, and still more preferably 0.05 MPa or more. Further, from the viewpoint of pressure resistance, the pressure is preferably 0.5 MPa or less, more preferably 0.25 MPa or less, and still more preferably 0.2 MPa or less.

From the viewpoint of reducing the amount of low molecular weight substance, the microfiltration is preferably performed at a flow rate of 10 mL/min or more and more preferably performed at a flow rate of 50 mL/min or more, and is preferably performed at a flow rate of 5,000 mL/min or less and more preferably performed at a flow rate of 1,000 mL/min or less.

The dialysis membrane treatment is performed using a dialysis membrane. The dialysis membrane usually has a molecular weight cut-off of $0.05 \times 10^4$ to $100 \times 10^4$ Da.

The molecular weight cut-off of the dialysis membrane is preferably $0.3 \times 10^4$ Da or more because the clogging of the membrane can be suppressed, and coloration can be efficiently reduced. The molecular weight cut-off is more preferably $0.5 \times 10^4$ Da or more, still more preferably $1.0 \times 10^4$ Da or more, further preferably $1.5 \times 10^4$ Da or more, still further preferably $2.0 \times 10^4$ Da or more, particularly preferably $3.0 \times 10^4$ Da or more, and most preferably $5.0 \times 10^4$ Da or more. The molecular weight cut-off may be $8.0 \times 10^4$ Da or more.

Further, from the viewpoint of reducing coloration, the molecular weight cut-off is preferably $20 \times 10^4$ Da or less, and more preferably $10 \times 10^4$ Da or less.

The molecular weight cut-off of the dialysis membrane can be measured by, for example, the same method as the ultrafiltration membrane.

Dialysis membrane treatment is preferably performed on the composition containing the fluoropolymer to efficiently remove a dimer and a trimer of a monomer forming the structural unit M3, a dimer and a trimer of a monomer forming a structural unit constituting the polymer α described below, and a dimer and a trimer of a monomer forming a structural unit constituting the water-soluble polymer described below from the composition containing the fluoropolymer. The molecular weight cut-off of the ultrafiltration membrane used at this time is preferably $0.3 \times 10^4$ Da or more and more preferably $0.5 \times 10^4$ Da or more, and is preferably $8.0 \times 10^4$ Da or less and more preferably $5.0 \times 10^4$ Da or less.

The material of the dialysis membrane is not limited, and examples include polyethylene, cellulose, polyacrylonitrile, polymethylmethacrylate, ethylene vinyl alcohol copolymers, polysulfone, polyamide, and polyester polymer alloy.

Specific examples of the dialysis membrane include Spectra/Por® Float-A-Lyzer, Tube-A-Lyzer, Dialysis tubing, 6 Diarysis tubing, and 7 Diarysis tubing manufactured by Spectrum Laboratories Inc.

Ultrafiltration, microfiltration, or dialysis membrane treatment is preferably performed at a temperature of 10° C. or higher. The temperature is more preferably 15° C. or higher, still more preferably 20° C. or higher, and particularly preferably 30° C. or higher. By adjusting the temperature within the above range, the amount of low molecular weight substance can be more efficiently reduced. The temperature is preferably 90° C. or lower, more preferably 80° C. or lower, still more preferably 70° C. or lower, and particularly preferably 60° C. or lower.

In the first production method of the present disclosure, water may be added or a pH adjuster may be added to the composition containing water and the fluoropolyrer to adjust the pH of the composition containing water and the fluoropolyrer, while performing ultrafiltration, microfiltration, or dialysis membrane treatment.

Accordingly, the step A may comprise the step of adding water to the composition containing water and the fluoropolymer, and water may be added in a stepwise or continuous manner. Further, the step A may comprise the step of adding a pH adjuster to the composition containing water and the fluoropolymer.

Among the ultrafiltration, the microfiltration, or the diafiltration membrane treatment, the ultrafiltration or the microfiltration is preferable, and the ultrafiltration is more preferable. The end point of the ultrafiltration, the microfiltration, or the dialysis membrane treatment is suitably determined, and is not limited. Further, in the ultrafiltration, the microfiltration, or the dialysis membrane treatment, in order to improve the durability of the filtration membrane, the membrane may be backwashed once per 1 to 24 hours as a rough guide during the filtration step.

By the first production method of the present disclosure, a composition containing the fluoropolymer and having a reduced content of low molecular weight substance can be obtained.

The present disclosure also provides a method for producing a composition, the method comprising a step A1 of performing ultrafiltration, microfiltration, dialysis membrane treatment, or a combination thereof on a composition containing water and a polymer (hereinafter also referred to as a "polymer α") in which the proportion of carbon atom-bonded hydrogen atoms replaced with fluorine atoms is 50% or more, which contains an ionic group, and which has an ion-exchange rate of 53 or less (hereinafter also referred to as the "second production method of the present disclosure").

The composition obtained by the second production method of the present disclosure may be an aqueous solution.

In the second production method of the present disclosure, the step A1 can be performed in the entirely same manner as the first production method of the present disclosure except that a composition containing a polymer α in which the proportion of carbon atom-bonded hydrogen atoms replaced with fluorine atoms is 50% or more, which contains an ionic group, and which has an ion-exchange rate of 53 or less is used.

The "proportion of carbon atom-bonded hydrogen atoms replaced with fluorine atoms" is obtained as the proportion of the number of fluorine atoms to the total number of hydrogen atoms bonded to carbon atoms and halogen atoms (including fluorine atoms) bonded to carbon atoms.

The polymer α is not limited, a polymer, among the above-described fluoropolymers, in which the proportion of carbon atom-bonded hydrogen atoms replaced with fluorine atoms is 50% or more, which contains an ionic group (an anionic group), and which has an ion exchange rate of 53 or less is usable, and a polymer, other than the above-described fluoropolymers, in which the proportion of carbon atom-bonded hydrogen atoms replaced with fluorine atoms is 50% or more, which contains an ionic group (an anionic group), and which has an ion exchange rate of 53 or less is also usable.

Examples of the polymer α include a polymer containing structural unit (I) based on a monomer represented by general formula (I). The polymer α preferably contains two or more structural units (I):

$$CX^1X^3=CX^2R-CZ^1Z^2-A^0 \quad (I)$$

wherein $X^1$ and $X^3$ are each independently F, Cl, H, or $CF_3$; $X^2$ is H, F, an alkyl group, or a fluorine-containing alkyl group; $A^0$ is an anionic group; R is a linking group; and $Z^1$ and $Z^2$ are each independently H, F, an alkyl group, or a fluorine-containing alkyl group.

$X^2$ is preferably F, Cl, H, or $CF_3$. Further, $Z^1$ and $Z^2$ are preferably F or $CF_3$, and more preferably one is F and the other is $CF_3$.

In the present disclosure, the anionic group includes a functional group that imparts an anionic group, e.g., an acid group such as —COOH and an acid base such as —COCNH$_4$, in addition to anionic groups such as a sulfate group and a carboxylate group. The anionic group is preferably a sulfate group, a carboxylate group, a phosphate group, a phosphonate group, a sulfonate group, or —C(CF$_3$)$_2$OM, wherein M is —H, a metal atom, —NR$^7_4$, imidazolium optionally having a substituent, pyridinium optionally having a substituent, or phosphonium optionally having a substituent, and $R^7$ is H or an organic group.

The polymer α may contain the structural unit (I) that is based solely on one monomer represented by the general formula (I), or may contain the structural unit (I) based on two or more monomers represented by the general formula (I).

R is a linking group. The "linking group" as used herein refers to a divalent linking group. The linking group may be a single bond and preferably contains at least one carbon atom, and the number of carbon atoms may be 2 or more, 4 or more, 8 or more, 10 or more, or 20 or more. The upper limit thereof is not limited, but may be 100 or less, and may be 50 or less, for example.

The linking group may be linear or branched, cyclic or acyclic, saturated or unsaturated, substituted or unsubstituted, and optionally contains one or more heteroatoms selected from the group consisting of sulfur, oxygen, and nitrogen, and optionally contains one or more functional groups selected from the group consisting of esters, amides, sulfonamides, carbonyls, carbonates, urethanes, ureas, and carbamates. The linking group may be free from carbon atoms and may be a catenary heteroatom such as oxygen, sulfur, or nitrogen.

R is preferably a catenary heteroatom such as oxygen, sulfur, or nitrogen, or a divalent organic group.

When R is a divalent organic group, the hydrogen atom bonded to the carbon atom may be replaced by a halogen other than fluorine, such as chlorine, and may or may not contain a double bond. Further, R may be linear or branched, and may be cyclic or acyclic. R may also contain a functional group (e.g., ester, ether, ketone, amine, halide, etc.).

R may also be a fluorine-free divalent organic group or a partially fluorinated or perfluorinated divalent organic group.

R may be, for example, a hydrocarbon group in which a fluorine atom is not bonded to a carbon atom, a hydrocarbon group in which some of the hydrogen atoms bonded to a carbon atom are replaced by fluorine atoms, or a hydrocarbon group in which all of the hydrogen atoms bonded to the carbon atoms are replaced by fluorine atoms, and these groups optionally contain an oxygen atom, optionally contain a double bond, and optionally contain a functional group.

R is preferably a hydrocarbon group having 1 to 100 carbon atoms that optionally contains an ether bond, wherein some or all of the hydrogen atoms bonded to the carbon atoms in the hydrocarbon group may be replaced by fluorine.

R is preferably at least one selected from —$(CH_2)_a$—, —$(CF_2)_a$—, —O—$(CF_2)_a$—, —$(CF_2)_a$—O—$(CF_2)_b$—, —O$(CF_2)_a$—O—$(CF_2)_b$—, —$(CF_2)_a$—[O—$(CF_2)_b$]$_c$—, —O$(CF_2)_a$—[O—$(CF_2)_b$]$_c$—, —[$(CF_2)_a$—O]$_b$—[$(CF_2)_c$—O]$_d$—, —O[$(CF_2)_a$—O]$_b$—[$(CF_2)_c$—O]$_d$—, —O—[$CF_2CF(CF_3)O]_a$— $(CF_2)_b$—, —[$CF_2CF(CF_3)O]_a$—, —[$CF(CF_3)CF_2O]_a$—, —$(CF_2)_aO$—[$CF(CF_3)CF_2O]_a$—, —$(CF_2)_a$—O— [$CF(CF_3)CF_2O]_a$— $(CF_2)_b$—, and combinations thereof.

In the formula, a, b, c, and d are independently at least 1 or more. a, b, c, and d may independently be 2 or more, 3 or more, 4 or more, 10 or more, or 20 or more. The upper limits of a, b, c, and d are 100, for example.

R is preferably a divalent group represented by the following general formula (r1):

wherein $X^6$ is each independently H, F, or $CF_3$; e is an integer of 0 to 3; f is an integer of 0 to 3; and g is 0 or 1, and is also preferably a divalent group represented by the following general formula (r2):

wherein $X^7$ is each independently H, F, or $CF_3$; e is an integer of 0 to 3; and g is 0 or 1.

Specific examples suitable for R include —$CF_2$—O—, —$CF_2$—O—$CF_2$—, —$CF_2$—O—$CH_2$—, —$CF_2$—O—$CH_2CF_2$—, —$CF_2$—O—$CF_2CF_2$—, —$CF_2$—O—$CF_2CH_2$—, —$CF_2$—O—$CF_2CF_2CH_2$—, —$CF_2$—O—$CF(CF_3)$—, —$CF_2$—O—$CF(CF_3)CF_2$—, —$CF_2$—O—$CF(CF_3)CF_2$—O—, —$CF_2$—O—$CF(CF_3)CF_2$—O—$CF_2$—, and —$CF_2$—O—$CF(CF_3)CH_2$—. In particular, R is preferably a perfluoroalkylene group optionally containing an oxygen atom, and, specifically, —$CF_2$—O—, —$CF_2$—O—$CF_2$—, —$CF_2$—O—$CF_2CF_2$—, —$CF_2$—O—$CF(CF_3)$—, —$CF_2$—O—$CF(CF_3)CF_2$—, or —$CF_2$—O—$CF(CF_3)CF_2$—O— is preferable.

—R—$CZ^1Z^2$— in the general formula (I) is preferably a divalent group represented by the following formula (s1):

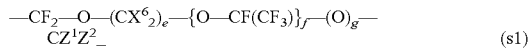

(wherein $X^6$ is each independently H, F, or $CF_3$; e is an integer of 0 to 3; f is an integer of 0 to 3; g is 0 or 1; and $Z^1$ and $Z^2$ are each independently H, F, an alkyl group, or a fluorine-containing alkyl group), and more preferably, in the formula (s1), $Z^1$ and $Z^2$ are F or $CF_3$, and further preferably one is F, and the other is $CF_3$.

Further, —R—$CZ^1Z^2$— in the general formula (I) is preferably a divalent group represented by the following formula (s2):

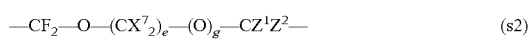

(wherein $X^7$ is each independently H, F, or $CF_3$; e is an integer of 0 to 3; g is 0 or 1; and $Z^1$ and $Z^2$ are each independently H, F, an alkyl group, or a fluorine-containing alkyl group), and more preferably, in the formula (s2), $Z^1$ and $Z^2$ are F or $CF_3$, and further preferably one is F, and the other is $CF_3$.

—R—$CZ^1Z^2$— in the above general formula (I) is preferably —$CF_2$—O—$CF_2$—, —$CF_2$—O—$CF(CF_3)$—, —$CF_2$—O—$C(CF_3)_2$—, —$CF_2$—O—$CF_2$—$CF_2$—, —$CF_2$—O—$CF_2$—$CF(CF_3)$—, —$CF_2$—O—$CF_2$—$C(CF_3)_2$—, —$CF_2$—O—$CF_2CF_2$—$CF_2$—, —$CF_2$—O—$CF_2CF_2$—$CF(CF_3)$—, —$CF_2$—O—$CF_2CF_2$—$C(CF_3)_2$—, —$CF_2$—O—$CF(CF_3)$—$CF_2$—, —$CF_2$—O—$CF(CF_3)$—$CF(CF_3)$—, —$CF_2$—O—$CF(CF_3)$—$C(CF_3)_2$—, —$CF_2$—O—$CF(CF_3)$—$CF_2$—, —$CF_2$—O—$CF(CF_3)CF(CF_3)$—, —$CF_2$—O—$CF(CF_3)CF_2$—$CF(CF_3)$—, —$CF_2$—O—$CF(CF_3)CF_2$—$C(CF_3)_2$—, —$CF_2$—O—$CF(CF_3)CF_2$—O—$CF_2$—, —$CF_2$—O—$CF(CF_3)CF_2$—O—$CF(CF_3)$—, or —$CF_2$—O—$CF(CF_3)CF_2$—O—$C(CF_3)_2$—, and more preferably —$CF_2$—O—$CF(CF_3)$—, —$CF_2$—O—$CF_2$—$CF(CF_3)$—, —$CF_2$—O—$CF_2CF_2$—$CF(CF_3)$—, —$CF_2$—O—$CF(CF_3)$—$CF(CF_3)$—, —$CF_2$—O—$CF(CF_3)$—$CF(CF_3)$—, or —$CF_2$—O—$CF(CF_3)CF_2$—O—$CF(CF_3)$—.

It is also preferable that the polymer α is highly fluorinated. Except for the anionic group (A°) such as a phosphate group moiety (such as $CH_2OP(O)$ $(OM)_2$) and a sulfate group moiety (such as $CH_2OS(O)_2OM$), 80% or more, 90% or more, 95% or more, or 100% of C—H bonds in the polymer α are replaced with C—F bonds. The proportion of carbon atom-bonded hydrogen atoms replaced with fluorine atoms in the polymer α is not limited, and is 50% or more, preferably 80% or more, more preferably 90% or more, still more preferably 95% or more, and particularly preferably 100%.

The polymer α also preferably has a C—F bond and does not have a C—H bond, in the portion excluding the anionic group (A°). In other words, in the general formula (I), $X^1$, $X^2$, and $X^3$ are all F, and R is preferably a perfluoroalkylene group having one or more carbon atoms; the perfluoroalkylene group may be either linear or branched, may be either cyclic or acyclic, and may contain at least one catenary heteroatom. The perfluoroalkylene group may have 2 to 20 carbon atoms or 4 to 18 carbon atoms.

The polymer α may be partially fluorinated. In other words, the polymer α also preferably has at least one hydrogen atom bonded to a carbon atom and at least one fluorine atom bonded to a carbon atom, in the portion excluding the anionic group (A°).

The anionic group (A°) may be —$SO_3M$, —$OSO_3M$, —COOM, —$SO_2NR'CH_2COOM$, —$CH_2OP(O)$ $(OM)_2$, [—$CH_2O]_2P(O)$ (OM), —$CH_2CH_2OP(O)$ $(OM)_2$, [—$CH_2CH_2O]_2P(O)$ (OM), —$CH_2CH_2OSO_3M$, —P(O) $(M)_2$, —$SO_2NR'CH_2CH_2OP(O)$ $(M)_2$, [—$SO_2NR'CH_2CH_2O]_2P(O)$ (OM), —$CH_2OSO_3M$, —$SO_2NR'CH_2CH_2OSO_3M$, or —$C(CF_3)_2CM$. Among these, —$SO_3M$, —COOM, or —P(O) $(OM)_2$ is preferable, —$SO_3M$ or —COOM is more preferable, and —COOM is still more preferable.

M is H, a metal atom, $NR^7_4$, imidazolium optionally having a substituent, pyridinium optionally having a substituent, or phosphonium optionally having a substituent, and $R^7$ is H or an organic group.

Examples of the metal atom include alkali metals (Group 1) and alkaline earth metals (Group 2), and preferred is Na, K, or Li.

M is preferably —H, a metal atom, or —$NR^7_4$, more preferably —H, an alkali metal (Group 1), an alkaline earth metal (Group 2), or —$NR^7_4$, still more preferably —H, —Na, —K, —Li, or —$NH_4$, further preferably —Na, —K, or —$NH_4$, particularly preferably —Na or —$NH_4$, and most preferably —$NH_4$.

In the polymer α, each structural unit (I) may have a different anionic group or may have the same anionic group.

The polymer α is also preferably a polymer containing a structural unit (Ia) based on a monomer represented by the following formula (Ia):

wherein A° is an anionic group; and Rf° is a perfluorinated divalent linking group which is perfluorinated and may be a linear or branched, cyclic or acyclic, saturated or unsaturated, substituted or unsubstituted, and optionally contains one or more heteroatoms selected from the group consisting of sulfur, oxygen, and nitrogen.

The polymer α is also preferably a polymer containing a structural unit (Ib) based on a monomer represented by the following formula (Ib):

$$CH_2=CH-O-Rf^0-A^0 \quad (Ib)$$

wherein $A^0$ is an anionic group, and $Rf^0$ is a perfluorinated divalent linking group as defined by formula (Ia).

The polymer α is also preferably a polymer containing a structural unit (Ic) based on a monomer represented by the following formula (Ic):

$$CH_2=CF-O-Rf^0-A^0 \quad (Ic)$$

wherein $A^0$ is an anionic group, and $Rf^0$ is a perfluorinated divalent linking group as defined by formula (Ia).

In a preferred embodiment, in the general formula (I), $A^0$ is a sulfate group. $A^0$ is, for example, $-CH_2OSO_3M$, $-CH_2CH_2OSO_3M$, or $-SO_2NR'CH_2CH_2OSO_3M$, wherein R' is H or an alkyl group having 1 to 4 carbon atoms, and M is the same as above.

When $A^0$ is a sulfate group, examples of the monomer represented by the general formula (I) include $CF_2=CF(OCF_2CF_2CH_2OSO_3M)$, $CH_2=CH((CF_2)_4CH_2OSO_3M)$, $CF_2=CF(O(CF_2)_4CH_2OSO_3M)$, $CF_2=CF(OCF_2CF(CF_3)CH_2OSO_3M)$, $CF_2=CF(OCF_2CF(CF_3)OCF_2CF_2CH_2OSO_3M)$, $CH_2=CH((CF_2)_4CH_2OSO_3M)$, $CF_2=CF(OCF_2CF_2SO_2N(CH_3)CH_2CH_2OSO_3M)$, $CH_2=CH(CF_2CF_2CH_2OSO_3M)$, $CF_2=CF(OCF_2CF_2CF_2CF_2SO_2N(CH_3)CH_2CH_2OSO_3M)$, and $CH_2=CH(CF_2CF_2CF_2CH_2OSO_3M)$. In the formula, M is the same as above.

In a preferred embodiment, in the general formula (I), $A^0$ is a sulfonate group. $A^0$ is, for example, $-SO_3M$, wherein M is the same as above.

When $A^0$ is a sulfonate group, examples of the monomer represented by the general formula (I) include $CF_2=CF(OCF_2CF_2SO_3M)$, $CF_2=CF(O(CF_2)_3SO_3M)$, $CF_2=CF(O(CF_2)_4SO_3M)$, $CF_2=CF(OCF_2CF(CF_3)SO_3M)$, $CF_2=CF(OCF_2CF(CF_3)OCF_2CF_2SO_3M)$, $CH_2=CH(CF_2CF_2SO_3M)$, $CF_2=CF(OCF_2CF(CF_3)OCF_2CF_2CF_2SO_3M)$, $CH_2=CH((CF_2)_4SO_3M)$, $CH_2=CH(CF_2CF_2SO_3M)$, and $CH_2=CH((CF_2)_3SO_3M)$. In the formula, M is the same as above.

In a preferred embodiment, in the general formula (I), $A^0$ is a carboxylate group. $A^0$ is, for example, $-COOM$ or $-SO_2NR'CH_2COOM$, wherein R' is H or an alkyl group having 1 to 4 carbon atoms, and M is the same as above.

When $A^0$ is a carboxylate group, examples of the monomer represented by the general formula (I) include $CF_2=CF(OCF_2CF_2COOM)$, $CF_2=CF(O(CF_2)_3COOM)$, $CF_2=CF(O(CF_2)_5COOM)$, $CF_2=CF(OCF_2CF(CF_3)COOM)$, $CF_2=CF(OCF_2CF(CF_3)O(CF_2)_nCOOM)$ (n is greater than 1), $CH_2=CH(CF_2CF_2COOM)$, $CH_2=CH((CF_2)_4COOM)$, $CH_2=CH(CF_2CF_2COOM)$, $CH_2=CH((CF_2)_3COOM)$, $CF_2=CF(OCF_2CF_2SO_2NR'\ CH_2COOM)$, $CF_2=CF(O(CF_2)_4SO_2NR'CH_2COOM)$, $CF_2=CF(OCF_2CF(CF_3)SO_2NR'CH_2COOM)$, $CF_2=CF(OCF_2CF(CF_3)OCF_2CF_2SO_2NR'\ CH_2COOM)$, $CH_2=CH(CF_2CF_2SO_2NR'\ CH_2COOM)$, $CF_2=CF(OCF_2CF(CF_3)OCF_2CF_2CF_2SO_2NR'\ CH_2COOM)$, $CH_2=CH((CF_2)_4SO_2NR'\ CH_2COOM)$, $CH_2=CH(CF_2CF_2SO_2NR'\ CH_2COOM)$, and $CH_2=CH((CF_2)_3SO_2NR'\ CH_2COOM)$. In the formula, R' is H or an alkyl group having 1 to 4 carbon atoms, and M is the same as above.

In a preferred embodiment, in the general formula (I), $A^0$ is a phosphate group. $A^0$ is, for example, $-CH_2OP(O)(OM)_2$, $[-CH_2O]_2P(O)(OM)$, $-CH_2CH_2OP(O)(OM)_2$, $[-CH_2CH_2O]_2P(O)(OM)$, $[-SO_2NR'CH_2CH_2O]_2P(O)(OM)$, or $-SO_2NR'CH_2CH_2OP(O)(OM)_2$, wherein R' is an alkyl group having 1 to 4 carbon atoms, and M is the same as above.

When $A^0$ is a phosphate group, examples of the monomer represented by the general formula (I) include $CF_2=CF(OCF_2CF_2CH_2OP(O)(OM)_2)$, $CF_2=CF(O(CF_2)_4CH_2OP(O)(OM)_2)$, $CF_2=CF(OCF_2CF(CF_3)CH_2OP(O)(OM)_2)$, $CF_2=CF(OCF_2CF(CF_3)OCF_2CF_2CH_2OP(O)(OM)_2)$, $CF_2=CF(OCF_2CF_2SO_2N(CH_3)CH_2CH_2OP(O)(OM)_2)$, $CF_2=CF(OCF_2CF_2CF_2CF_2SO_2N(CH_3)CH_2CH_2OP(O)(OM)_2)$, $CH_2=CH(CF_2CF_2CH_2OP(O)(OM)_2)$, $CH_2=CH((CF_2)_4CH_2OP(O)(OM)_2)$, $CH_2=CH(CF_2CF_2CH_2OP(O)(OM)_2)$, and $CH_2=CH((CF_2)_3CH_2OP(O)(OM)_2)$. In the formula, M is the same as above.

In a preferred embodiment, in the general formula (I), $A^0$ is preferably a phosphonate group. When $A^0$ is a phosphonate group, examples of the monomer represented by the general formula (I) include $CF_2=CF(OCF_2CF_2P(O)(OM)_2)$, $CF_2=CF(O(CF_2)_4P(O)(OM)_2)$, $CF_2=CF(OCF_2CF(CF_3)P(O)(OM)_2)$, $CF_2=CF(OCF_2CF(CF_3)OCF_2CF_2P(O)(OM)_2)$, $CH_2=CH(CF_2CF_2P(O)(OM)_2)$, $CH_2=CH((CF_2)_4P(O)(OM)_2)$, $CH_2=CH(CF_2CF_2P(O)(OM)_2)$, and $CH_2=CH((CF_2)_3P(O)(OM)_2)$, wherein M is the same as above.

Examples of the polymer α include a polymer containing the structural unit M3 derived from a monomer represented by the following general formula (1):

$$CX_2=CY(-CZ_2-O-Rf-A) \quad (1)$$

wherein X is the same or different and is $-H$ or $-F$; Y is $-H$, $-F$, an alkyl group, or a fluorine-containing alkyl group; Z is the same or different and is $-H$, $-F$, an alkyl group, or a fluoroalkyl group; Rf is a fluorine-containing alkylene group having 1 to 40 carbon atoms or a fluorine-containing alkylene group having 2 to 100 carbon atoms and having an ether bond; A is $-COOM$, $-SO_3M$, $-OSO_3M$, or $C(CF_3)_2CM$, wherein M is $-H$, a metal atom, $-NR^7_4$, imidazolium optionally having a substituent, pyridinium optionally having a substituent, or phosphonium optionally having a substituent, and $R^7$ is H or an organic group; provided that at least one of X, Y, and Z contains a fluorine atom.

The structural unit M3 contained in the polymer α is the same as the structural unit M3 contained in the fluoropolymer described above, and a preferable configuration is also the same.

The polymer α is also preferably a polymer containing a structural unit (2) based on a monomer represented by general formula (2):

$$CX_2=CY(-O-Rf-A) \quad (2)$$

wherein X is the same or different and is $-H$ or $-F$; Y is $-H$, $-F$, an alkyl group, or a fluorine-containing alkyl group; Rf is a fluorine-containing alkylene group having 1 to 40 carbon atoms or a fluorine-containing alkylene group having 2 to 100 carbon atoms and having an ether bond; and A is as described above.

In the general formula (2), each X is —H or —F. X may be both —F, or at least one thereof may be —H. For example, one thereof may be —F and the other may be —H, or both may be —H.

In the general formula (2), Y is —H, —F, an alkyl group, or a fluorine-containing alkyl group. The alkyl group is an alkyl group free from fluorine atoms and may have one or more carbon atoms. The alkyl group preferably has 6 or less carbon atoms, more preferably 4 or less carbon atoms, and still more preferably 3 or less carbon atoms. The fluorine-containing alkyl group is an alkyl group containing at least one fluorine atom, and may have one or more carbon atoms. The fluorine-containing alkyl group preferably has 6 or less carbon atoms, more preferably 4 or less carbon atoms, and still more preferably 3 or less carbon atoms. Y is preferably —H, —F, or —CF$_3$, and more preferably —F.

In the general formula (2), at least one of X and Y preferably contains a fluorine atom. For example, X may be —H, and Y and Z may be —F.

In the general formula (2), Rf is a fluorine-containing alkylene group having 1 to 40 carbon atoms or a fluorine-containing alkylene group having 2 to 100 carbon atoms and having an ether bond. The fluorine-containing alkylene group having 2 to 100 carbon atoms and having an ether bond is an alkylene group which does not include a structure wherein an oxygen atom is an end and which contains an ether bond between carbon atoms.

The fluorine-containing alkylene group of Rf preferably has 2 or more carbon atoms. The fluorine-containing alkylene group also preferably has 30 or less carbon atoms, more preferably 20 or less carbon atoms, and still more preferably 10 or less carbon atoms. Examples of the fluorine-containing alkylene group include —CF$_2$—, —CH$_2$CF$_2$—, —CF$_2$CF$_2$—, —CF$_2$CH$_2$—, —CF$_2$CF$_2$CH$_2$—, —CF(CF$_3$)—, —CF(CF$_3$)CF$_2$—, and —CF(CF$_3$)CH$_2$—. The fluorine-containing alkylene group is preferably a perfluoroalkylene group.

The monomer represented by the general formula (2) is preferably at least one selected from the group consisting of monomers represented by the following general formulas (2a), (2b), (2c), (2d), and (2e):

$$CF_2=CF-O-(CF_2)_{n1}\text{-}A \qquad (2a)$$

wherein n1 represents an integer of 1 to 10, and A is as defined above;

$$CF_2=CF-O-(CF_2C(CF_3)F)_{n2}\text{-}A \qquad (2b)$$

wherein n2 represents an integer of 1 to 5, and A is as defined above;

$$CF_2=CF-O-(CFX^1)_{n3}\text{-}A \qquad (2c)$$

wherein X$^1$ represents F or CF$_3$; n3 represents an integer of 1 to 10; and A is as defined above;

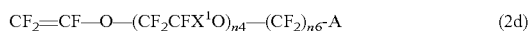
$$CF_2=CF-O-(CF_2CFX^1O)_{n4}-(CF_2)_{n6}\text{-}A \qquad (2d)$$

wherein n4 represents an integer of 1 to 10; n6 represents an integer of 1 to 3; and A and X$^1$ are as defined above; and

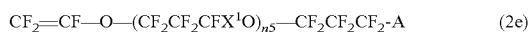
$$CF_2=CF-O-(CF_2CF_2CFX^1O)_{n5}-CF_2CF_2CF_2\text{-}A \qquad (2e)$$

wherein n5 represents an integer of 0 to 10, and A and X$^1$ are as defined above.

In the general formula (2a), n1 is preferably an integer of 5 or less, and more preferably an integer of 2 or less.

Examples of the monomer represented by the general formula (2a) include CF$_2$=CF—O—CF$_2$COOM, CF$_2$=CF(OCF$_2$CF$_2$COOM), and CF$_2$=CF(OCF$_2$CF$_2$CF$_2$COOM), wherein M is as defined above.

In the general formula (2b), n2 is preferably an integer of 3 or less from the viewpoint of water solubility.

In the general formula (2c), n3 is preferably an integer of 5 or less from the viewpoint of water solubility, A is preferably —COOM, and M is preferably H or NH$_4$.

In the general formula (2d), X$^1$ is preferably —CF$_3$ from the viewpoint of water solubility, n4 is preferably an integer of 5 or less from the viewpoint of water solubility, A is preferably —COOM, and M is preferably H or NH$_4$.

Examples of the monomer represented by the general formula (2d) include CF$_2$=CFOCF$_2$CF(CF$_3$)OCF$_2$CF$_2$COOM, CF$_2$=CFOCF$_2$CF(CF$_3$)OCF$_2$COOM, and CF$_2$=CFOCF$_2$CF(CF$_3$)OCF$_2$CF$_2$CF$_2$COOM (wherein M represents H, NH$_4$, or an alkali metal).

In the general formula (2e), n5 is preferably an integer of 5 or less from the viewpoint of water solubility, A is preferably —COOM, and M is preferably H or NH$_4$.

Examples of the monomer represented by the general formula (2e) include CF$_2$=CFOCF$_2$CF$_2$CF$_2$COOM (wherein M represents H, NH$_4$, or an alkali metal).

The polymer α is also preferably a polymer containing a structural unit (3) based on a monomer represented by general formula (3):

$$CX_2=CY(-Rf\text{-}A) \qquad (3)$$

wherein X is the same or different and is —H or —F; Y is —H, —F, an alkyl group, or a fluorine-containing alkyl group; Rf is a fluorine-containing alkylene group having 1 to 40 carbon atoms or a fluorine-containing alkylene group having 2 to 100 carbon atoms and having an ether bond; and A is as described above.

The fluorine-containing alkylene group having 2 to 100 carbon atoms and having an ether bond is an alkylene group which does not include a structure wherein an oxygen atom is an end and which contains an ether bond between carbon atoms.

In the general formula (3), Rf is preferably a fluorine-containing alkylene group having 1 to 40 carbon atoms. In the general formula (3), at least one of X and Y preferably contains a fluorine atom.

The monomer represented by the general formula (3) is preferably at least one selected from the group consisting of a monomer represented by general formula (3a):

$$CF_2=CF-(CF_2)_{n1}\text{-}A \qquad (3a)$$

wherein n1 represents an integer of 1 to 10, and A is as defined above; and a monomer represented by general formula (3b):

$$CF_2=CF-(CF_2C(CF_3)F)_{n2}\text{-}A \qquad (3b)$$

wherein n2 represents an integer of 1 to 5, and A is as defined above.

In general formulas (3a) and (3b), A is preferably —SO$_3$M or —COOM, and M is preferably H, a metal atom, NR$^7$$_4$, imidazolium optionally having a substituent, pyridinium optionally having a substituent, or phosphonium optionally having a substituent. R$^7$ represents H or an organic group.

In the general formula (3a), n1 is preferably an integer of 5 or less, and more preferably an integer of 2 or less. A is preferably —COOM, and M is preferably H or NH$_4$.

Examples of the monomer represented by the general formula (3a) include CF$_2$=CFCF$_2$COOM, wherein M is as defined above.

In the general formula (3b), n2 is preferably an integer of 3 or less from the viewpoint of water solubility, A is preferably —COOM, and M is preferably H or NH$_4$.

The polymer α is preferably at least one selected from the group consisting of a polymer containing the structural unit M3, a polymer containing the structural unit (2), and a polymer containing the structural unit (3), and is more preferably a polymer containing the structural unit M3.

Examples of the polymer α also include a polymer α containing a structural unit (II) based on a monomer represented by general formula (II). The polymer α preferably contains two or more structural units (II):

$$CX^1X^3=CX^2R^{II}(-CZ^1Z^2-A^0)_{nII} \tag{II}$$

wherein $X^1$, $X^2$, $X^3$, $A^0$, $Z^1$, and $Z^2$ are as defined above, $R^{II}$ is a linking group having a valence of (nII+1), and nII is an integer of 2 or more.

nII is an integer of 2 or more, and preferably 2. $Z^1$, $Z^2$, and $A^0$ may be the same or different.

Examples of the monomer represented by the general formula (II) include a monomer represented by general formula (1-II) and a monomer represented by general formula (2-II):

$$CF_2=CF-CF_2-O-Q^{F1}-CF(-Q^{F2}-CZ^1Z^2-A)_2 \tag{1-II}$$

wherein $Z^1$, $Z^2$, and A are as defined above, and $Q^{F1}$ and $Q^{F2}$ are the same or different and are a single bond, a fluorine-containing alkylene group optionally containing an ether bond between carbon atoms, or a fluorine-containing oxyalkylene group optionally containing an ether bond between carbon atoms; and $$CF_2=CF-O-Q^{F1}-CF(-Q^{F2}-CZ^1Z^2-A)_2 \tag{2-II}$$

wherein $Z^1$, $Z^2$, A, $Q^{F1}$, and $Q^{F2}$ are as defined above.

Examples of the monomer represented by the general formula (II) include:

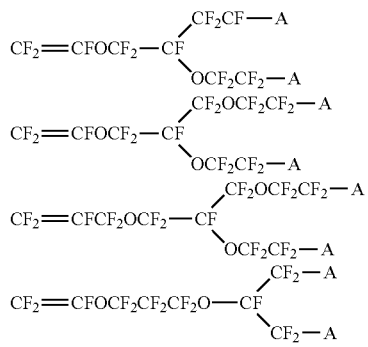

The polymer α may contain a structural unit based on a fluorine-containing monomer based on trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (FVE), $CH_2=CFCF_3$, $CHF=CHCF_3$ (E form), $CHF=CHCF_3$ (Z form), or the like (provided that the monomers represented by the general formula (I) and the general formula (II) are excluded).

The polymer α may also contain a structural unit based on a fluorine-free monomer. The fluorine-free monomer is a monomer having a radically polymerizable, ethylenically unsaturated bond, such as an acrylic acid ester, a methacrylic acid ester, an unsaturated carboxylic acid, a hydrolyzable silyl group-containing monomer, a hydroxyl group-containing alkyl vinyl ether, a carboxylic acid vinyl ester, or an α-olefin. In particular, the fluorine-free monomer is preferably at least one selected from the group consisting of an acrylic acid ester, a methacrylic acid ester, an unsaturated carboxylic acid, and a hydrolyzable silyl group-containing monomer.

The fluorine-free monomer is more preferably at least one monomer selected from the group consisting of an acrylic acid ester and a methacrylic acid ester, an unsaturated carboxylic acid, and at least one selected from the group consisting of hydrolyzable silyl group-containing monomers.

In addition, a monomer having a radically polymerizable, ethylenically unsaturated bond may be used in combination.

The acrylic acid ester or the methacrylic acid ester is preferably an acrylic acid alkyl ester having an alkyl group with 1 to 10 carbon atoms or a methacrylic acid alkyl ester having an alkyl group with 1 to 10 carbon atoms. Examples of the acrylic acid alkyl ester and the methacrylic acid alkyl ester include (meth)acrylic acid alkyl esters such as methyl acrylate, ethyl acrylate, n-propyl acrylate, isopropyl acrylate, n-butyl acrylate, methyl methacrylate, n-propyl methacrylate, ethyl methacrylate, n-butyl methacrylate, isopropyl methacrylate, 2-ethylhexyl acrylate, 2-ethylhexyl methacrylate, cyclohexyl acrylate, and cyclohexyl methacrylate. Further, the acrylic acid alkyl ester or the methacrylic acid alkyl ester may be a hydroxyl group-containing acrylic monomer having a hydroxyl group and a (meth)acryloyl group within the molecule, such as 2-hydroxyethyl acrylate, 2-hydroxypropyl acrylate, 4-hydroxybutyl acrylate, 2-hydroxyethyl methacrylate, 2-hydroxypropyl methacrylate, or 4-hydroxybutyl methacrylate.

One of these acrylic acid esters and methacrylic acid esters may be used alone, or two or more may be used in combination, and n-butyl acrylate and methyl methacrylate are preferable.

The fluorine-free monomer in particular is preferably at least one (meth)acrylic acid alkyl ester selected from the group consisting of methyl methacrylate, n-butyl acrylate, 2-ethylhexyl methacrylate, and cyclohexyl methacrylate. Neither the acrylic acid ester nor the methacrylic acid ester contains a hydrolyzable silyl group.

The acrylic acid ester or the methacrylic acid ester is still more preferably a combination of n-butyl acrylate and methyl methacrylate or a combination of n-butyl acrylate, methyl methacrylate, and 2-ethylhexyl methacrylate, and is particularly preferably a combination of n-butyl acrylate, methyl methacrylate, and 2-ethylhexyl methacrylate. In addition, it is also preferable to combine a hydroxyl group-containing acrylic monomer having a hydroxyl group and a (meth)acryloyl group.

Specific examples of the unsaturated carboxylic acid include acrylic acid, methacrylic acid, vinyl acetate, crotonic acid, cinnamic acid, 3-allyloxypropionic acid, 3-(2-allyloxyethoxycarbonyl)propionic acid, itaconic acid, itaconic acid monoester, maleic acid, maleic acid monoester, maleic anhydride, fumaric acid, fumaric acid monoester, vinyl phthalate, vinyl pyromellitate, and undecylenic acid. In particular, from the viewpoint that homopolymerizability is low so that a homopolymer is unlikely formed, and that introduction of a carboxyl group is readily controlled, at least one selected from the group consisting of acrylic acid, methacrylic acid, vinyl acetate, crotonic acid, itaconic acid, maleic acid, maleic acid monoester, fumaric acid, fumaric acid monoester, 3-allyloxypropionic acid, and undecylenic acid is preferable.

Examples of the hydrolyzable silyl group-containing monomer include $CH_2=CHCOO(CH_2)_3Si(OCH_3)_3$, $CH_2=CHCOO(CH_2)_3Si(CH_3)(OCH_3)_2$, $CH_2=CHCOO(CH_2)_3Si(OC_2H_5)_3$, $CH_2=CHCOO(CH_2)_3Si(CH_3)$ $(OC_2H_5)_2$, $CH_2=C(CH_3)COO(CH_2)_3Si(OCH_3)_3$, $CH_2=C(CH_3)COO(CH_2)_3Si(CH_3)(OCH_3)_2$, $CH_2=C(CH_3)COO(CH_2)_3Si(OC_2H_5)_3$, $CH_2=C(CH_3)COO(CH_2)_3Si(CH_3)(OC_2H_5)_2$, $CH_2=C(CH_3)COO(CH_2)_2O(CH_2)_3Si(OCH_3)_3$, $CH_2=C(CH_3)COO(CH_2)_2(CH_2)_3Si(CH_3)(OCH_3)_2$, $CH_2=C(CH_3)COO(CH_2)_{11}Si(OCH_3)_3$, and $CH_2=C(CH_3)COO(CH_2)_{11}Si(CH_3)(OCH_3)_2$. One of these hydrolyzable silyl group-containing monomers may be used alone, or two or more may be used in combination.

The hydrolyzable silyl group-containing monomer in particular is preferably at least one selected from the group consisting of γ-methacryloxypropyltrimethoxysilane, γ-methacryloxypropylmethyldimethoxysilane, γ-methacryloxypropyltriethoxysilane, and γ-methacryloxypropylmethyldiethoxysilane, and is more preferably γ-methacryloxypropyltriethoxysilane.

Examples of the hydroxyl group-containing alkyl vinyl ether include 2-hydroxyethyl vinyl ether, 3-hydroxypropyl vinyl ether, 2-hydroxypropyl vinyl ether, 2-hydroxy-2-methylpropyl vinyl ether, 4-hydroxybutyl vinyl ether, 4-hydroxy-2-methylbutyl vinyl ether, 5-hydroxypentyl vinyl ether, 6-hydroxyhexyl vinyl ether, 2-hydroxyethyl allyl ether, 4-hydroxybutyl allyl ether, and glycerol monoallyl ether. In terms of excellent polymerization reactivity, at least one selected from the group consisting of 4-hydroxybutyl vinyl ether and 2-hydroxyethyl vinyl ether is preferable.

Examples of the carboxylic acid vinyl ester include vinyl acetate, vinyl propionate, vinyl butyrate, vinyl isobutyrate, vinyl pivalate, vinyl caproate, vinyl versatate, vinyl laurate, vinyl stearate, vinyl cyclohexylcarboxylate, vinyl benzoate, and vinyl para-t-butylbenzoate.

Examples of the α-olefin include ethylene, propylene, n-butene, isobutene, and styrene.

In the polymer α, the content of the structural unit (I) is preferably 50% by mass or more, more preferably 60% by mass or more, still more preferably 70% by mass or more, further preferably 80% by mass or more, still further preferably 90% by mass or more, particularly preferably 95% by mass or more, and most preferably 99% by mass or more.

In the polymer α, the content of the structural unit M3 is preferably 50% by mass or more, more preferably 60% by mass or more, still more preferably 70% by mass or more, further preferably 80% by mass or more, still further preferably 90% by mass or more, particularly preferably 95% by mass or more, and most preferably 99% by mass or more.

In the polymer α, the total content of the structural unit based on a fluorine-containing monomer and the structural unit based on a fluorine-free monomer is preferably 50% by mass or less, more preferably 40% by mass or less, still more preferably 30% by mass or less, further preferably 20% by mass or less, still further preferably 10% by mass or less, particularly preferably 5% by mass or less, and most preferably 1% by mass or less.

The number average molecular weight of the polymer α is preferably $0.1×10^4$ or more, more preferably $0.2×10^4$ or more, still more preferably $0.3×10^4$ or more, further preferably $0.4×10^4$ or more, still further preferably $0.5×10^4$ or more, particularly preferably $1.0×10^4$ or more, very particularly preferably $3.0×10^4$ or more, and most preferably $3.1×10^4$ or more. The number average molecular weight is preferably $75.0×10^4$ or less, more preferably $50.0×10^4$ or less, still more preferably $40.0×10^4$ or less, still further preferably $30.0×10^4$ or less, and particularly preferably $20.0×10^4$ or less.

When the number average molecular weight is excessively low, dispersibility is decreased, and possibly the composition cannot be used as a dispersant. When the number average molecular weight is excessively high, viscosity is increased, and handling may become troublesome.

The weight average molecular weight of the polymer α is preferably $0.2×10^4$ or more, more preferably $0.4×10^4$ or more, still more preferably $0.6×10^4$ or more, further preferably $0.8×10^4$ or more, particularly preferably $1.0×10^4$ or more, more particularly preferably $5.0×10^4$ or more, still particularly preferably $10.0×10^4$ or more, still further preferably $15.0×10^4$ or more, very particularly preferably $20.0×10^4$ or more, and most preferably $25.0×10^4$ or more. The weight average molecular weight is preferably $150.0×10^4$ or less, more preferably $100.0×10^4$ or less, still more preferably $60.0×10^4$ or less, particularly preferably $50.0×10^4$ or less, and further preferably $40.0×10^4$ or less.

The number average molecular weight and the weight average molecular weight are molecular weight values calculated by gel permeation chromatography (GPC) using monodisperse polyethylene oxide (PEO) and polyethylene glycol (PEG) manufactured by Tosoh Corporation and Agilent as standards. Further, when measurement by GPC is not possible, the number average molecular weight of the polymer α can be determined by the correlation between the number average molecular weight calculated from the number of terminal groups obtained by NMR, FT-IR, or the like, and the melt flow rate. The melt flow rate can be measured in accordance with JIS K 7210.

The polymer α is preferably a water-soluble polymer.

The polymer α has an ion exchange rate (IXR) of 53 or less. The IXR is preferably 0.5 or more, more preferably 1 or more, still more preferably 3 or more, further preferably 4 or more, still further preferably 5 or more, and particularly preferably 8 or more. The IXR is preferably 43 or less, more preferably 33 or less, and still more preferably 23 or less. In the polymer α, the ionic groups (anionic groups) are typically distributed along the polymer backbone. The polymer α contains the polymer backbone together with a repeating side chain bonded to this backbone, and this side chain preferably has an ionic group.

The polymer α preferably contains an ionic group (anionic group) having a pKa of less than 10, and more preferably less than 7. The ionic group of the polymer α is preferably selected from the group consisting of sulfonate, carboxylate, phosphonate, phosphate, and a mixture thereof.

The terms "sulfonate, carboxylate, phosphonate, and phosphate" are intended to refer to the respective salts or the respective acids that can form salts. A salt when used is preferably an alkali metal salt or an ammonium salt. A preferable ionic group is a sulfonate group.

In the composition containing the polymer α, the concentration of the polymer α is not limited and may be, for example, 0.1 to 20% by mass.

The concentration of the polymer α is preferably 18.0% by mass or less because the efficiency of removing a low molecular weight substance is more increased. The concentration is more preferably 15% by mass or less, still more preferably 12% by mass or less, and particularly preferably 10% by mass or less. When the concentration of the polymer α is within the above range, a low molecular weight substance can be more efficiently removed. The concentration of the polymer α is preferably 0.5% by mass or more, more preferably 1.0% by mass or more, still more preferably 1.2% by mass or more, and particularly preferably 1.5% by mass or more.

The composition containing the polymer α may solely contain one polymer α, or may contain two or more different polymers α.

The composition containing the polymer α preferably has a pH of 0 to 11, and more preferably 0.5 to 8.0. The pH can be adjusted by using a pH adjuster. The pH adjuster may be an acid or an alkali, such as a phosphoric acid salt, sodium hydroxide, potassium hydroxide, or aqueous ammonia.

It is also preferable that the second production method of the present disclosure comprises the step of adjusting the pH of the composition containing the polymer α to 1.0 to 7.0 before the step A1.

The composition containing the polymer α can be obtained by a known polymerization method described above from which the polymer α is obtained. It is also one preferable embodiment that the second production method of the present disclosure comprises the step of polymerizing a monomer to obtain the polymer α. The monomer is suitably selected from monomers constituting the polymer α described above. The step of obtaining the polymer α is preferably performed in an aqueous medium. That is to say, the second production method of the present disclosure also preferably comprises the step of polymerizing a monomer represented by general formula (1) in an aqueous medium to obtain a composition containing the polymer α.

The composition containing the polymer α may be a composition directly obtained from polymerization, may be what is obtained after diluting or concentrating a composition directly obtained from polymerization, or may be what is obtained after performing dispersion stabilization treatment or the like. In order to facilitate ultrafiltration, microfiltration, or dialysis membrane treatment, it is also preferable to adjust the viscosity of the composition containing the polymer α by these treatments.

The viscosity of the composition containing the polymer α used in the step A1 is preferably 25 mPa·s or less because ultrafiltration, microfiltration, or dialysis membrane treatment is facilitated. The viscosity of the composition can be adjusted by, for example, a method involving adjusting the number average molecular weight of the polymer α, a method involving adjusting the concentration of the polymer α in the composition, or a method involving adjusting the temperature of the composition.

Due to the polymerization, a low molecular weight substance is usually produced as a by-product. In the second production method of the present disclosure, the low molecular weight substance can be removed by performing a treatment such as ultrafiltration on the composition containing the polymer α.

The composition containing the polymer α used in the step A1 may contain a low molecular weight substance, and, for example, the content of the low molecular weight substance is preferably more than 5.0%, more preferably 5.5% or more, still more preferably 6.0% or more, or more than 2.0% based on the polymer α.

Examples of the low molecular weight substance include a compound having a molecular weight of 700 or more and 3,000 or less, a compound having a molecular weight of 400 or more and 3,000 or less, a compound having a molecular weight of 700 or more and less than 10,000, a dimer and a trimer of a monomer forming the structural unit M3, a dimer and a trimer of a monomer forming a structural unit constituting the polymer α described below, and a dimer and a trimer of a monomer forming a structural unit constituting the water-soluble polymer described below.

The content of the low molecular weight substance is a value calculated from the peak area of GPC and/or a value calculated by liquid chromatography-mass spectrometry (LC/MS/MS) measurement.

By using the second production method of the present disclosure, a dimer and a trimer of a monomer forming a structural unit constituting the polymer α can also be removed from the composition containing the polymer α.

The dimer and the trimer are preferably a dimer and a trimer of the monomer represented by the general formula (I) (hereinafter also referred to as a monomer (I)). As for the monomer (I) represented by the general formula (I), the dimer and the trimer may each be a polymer formed from one monomer (I) or may be a copolymer formed from two or more monomers (I) having different structures. As for the monomer forming a suitable structural unit constituting the polymer α, examples of the dimer and the trimer include a dimer and a trimer of the above-described monomer.

As described above, the composition containing the polymer α can be produced by, for example, polymerizing the monomer (I).

The composition obtained by polymerizing the monomer (I) usually contains, as polymers of the monomer (I), a dimer and a trimer in a total amount of more than 1.0% based on the mass of the polymers of the monomer (I). The content of the dimer and the trimer in the polymers of the monomer (I) may be, for example, 2.0% by mass or more, may be 3.0% by mass or more, may be 30.0% by mass or less, and may be 20.0% by mass or less based on the polymers of the monomer (I). The content of the dimer and trimer in the composition can be determined by performing a gel permeation chromatography (GPC) analysis on the composition and calculating the total proportion of the peak areas (area percentages) of the dimer and the trimer to the total area of all peaks of the chromatogram obtained by the GPC analysis.

Previously, it was not known that the polymerization of the monomer (I) produces a dimer and a trimer of the monomer (I) and, as a result, the dimer and the trimer of the monomer (I) are contained in the polymer α. The mechanism by which the dimer and the trimer of the monomer (I) are produced is not necessarily clear, but it is conjectured that by the polymerization reaction in the polymerization system which is composed mostly of the monomer (I) among the monomers present in the polymerization system in particular, dimerization and trimerization of the monomer (I) occur with non-negligible frequency. The presence of the dimer and the trimer of the monomer (I) in the polymer α was discovered for the first time in the present disclosure, and it was found for the first time that the dimer and the trimer of the monomer (I) in the polymer α can be highly efficiently removed from the polymer α by at least one means selected from the group consisting of ultrafiltration, microfiltration, and dialysis membrane treatment.

When removing the dimer and the trimer, usually the unreacted monomer (I) is also removed from the composition at the same time.

By removing the dimer and the trimer from the composition containing the dimer and the trimer, a composition substantially free from the dimer and the trimer is obtained.

The content of the dimer and the trimer in the composition obtained by the second production method of the present disclosure is preferably 1.0% by mass or less, more preferably 0.1% by mass or less, still more preferably 0.01% by mass or less, particularly preferably 0.001% by mass or less, and most preferably 0.0001% by mass or less based on the polymer α.

The content of the dimer and trimer in the composition can be determined by performing a gel permeation chromatography (GPC) analysis on the composition and calculating the total proportion of the peak areas (area percentages) of the dimer and the trimer to the total area of all peaks of the chromatogram obtained by the GPC analysis.

Further, when the content of the dimer and the trimer in the composition is less than 0.5% by mass based on the polymer α, the content can be determined by liquid chromatography-mass spectrometry (LC/MS/MS) measurement.

Specifically, a composition having five or more content levels of the monomer (I) is prepared, the LC/MS/MS analysis is performed with respect to each content, the relationship between a content and an area relative to that content (the integral value of the peak) is plotted, and a calibration curve of the monomer (I) is created. Moreover, calibration curves of the dimer and the trimer of the monomer (I) are created from the calibration curve of the monomer (I).

Methanol is added to the polymer α to prepare a mixture, and an extract (supernatant) is recovered from the mixture by centrifugation, and the resulting extract is subjected to the LC/MS/MS analysis.

Then, using the calibration curves, the chromatographic area (the integral value of peaks) of the dimer and the trimer of the monomer (I) can be converted to the content of the dimer and the trimer.

The present invention also relates to a method for producing a composition, the method comprising a step A2 of performing ultrafiltration, microfiltration, dialysis membrane treatment, or a combination thereof on a composition containing water and a water-soluble polymer in which a proportion of carbon atom-bonded hydrogen atoms replaced with fluorine atoms is 50% or more (hereinafter also referred to as the "third production method of the present disclosure").

The composition obtained by the third production method of the present disclosure may be an aqueous solution.

In the third production method of the present disclosure, the step A2 can be performed in the entirely same manner as the first production method of the present disclosure except that a composition containing water and a water-soluble polymer in which the proportion of carbon atom-bonded hydrogen atoms replaced with fluorine atoms is 50% or more is used.

In the step A2, ultrafiltration, microfiltration, or dialysis membrane treatment is preferably performed at a temperature of 10° C. or higher. The temperature is more preferably 15° C. or higher, still more preferably 20° C. or higher, and particularly preferably 30° C. or higher. By adjusting the temperature within the above range, the low molecular weight substance can be more efficiently reduced. The temperature is preferably 90° C. or lower, more preferably 80° C. or lower, still more preferably 70° C. or lower, and particularly preferably 60° C. or lower.

The ultrafiltration is preferably performed using an ultrafiltration membrane having a molecular weight cut-off of $1.5 \times 10^4$ Da or more.

The water-soluble polymer is not limited, and, for example, a water-soluble polymer in which the proportion of carbon atom-bonded hydrogen atoms replaced with fluorine atoms is 50% or more can be used among the fluoropolymers described above, and a water-soluble polymer in which the proportion of carbon atom-bonded hydrogen atoms replaced with fluorine atoms is 50% or more can be used among the polymers α described above.

The present disclosure also relates to a composition containing water and a fluoropolymer that is a polymer containing a structural unit M3 derived from a monomer represented by general formula (1):

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —SO$_3$M, —OSO$_3$M, or —C(CF$_3$)$_2$OM, wherein M is —H, a metal atom, —NR$^7_4$, imidazolium optionally having a substituent, pyridinium optionally having a substituent, or phosphonium optionally having a substituent, and R$^7$ is H or an organic group; provided that at least one of X, Y, and Z contains a fluorine atom, wherein a content of a compound having a molecular weight of 700 or more and 3,000 or less is 3.5% or less based on the fluoropolymer (hereinafter referred to the "first composition of the present disclosure").

The first composition of the present disclosure may be an aqueous solution.

In the first composition of the present disclosure, the content of a compound having a molecular weight of 400 or more and 3,000 or less is preferably 3.7% or less based on the fluoropolymer.

Also, in the first composition of the present disclosure, the content of a compound having a molecular weight of 700 or more and less than 10,000 is preferably 5.0% or less based on the fluoropolymer.

Due to the reduced amount of low molecular weight substance, the first composition of the present disclosure can improve dispersibility (property of dispersing other components) when used as a dispersant in a polymer dispersion.

The coating agent obtained from the first composition of the present disclosure has excellent transparency, water repellency, and antireflection properties.

The first composition of the present disclosure can be preferably produced by the first production method of the present disclosure.

The first composition of the present disclosure contains water. The water content is not limited, and is preferably such an amount that the fluoropolymer can be dispersed or dissolved.

Examples of the fluoropolyrer in the first composition of the present disclosure include what is described with respect to the first production method of the present disclosure. Also, suitable embodiments can all be adopted.

For example, in the general formula (1), at least one X may be —H, or both may be —H. Rf is preferably a fluorine-containing alkylene group having 1 to 10 carbon atoms or a fluorine-containing alkylene group having 2 to 12 carbon atoms and having an ether bond. A is preferably —COOM, and M is preferably —H, —Na, —K, —Li, or —NH$_4$.

The structural unit M3 is preferably, for example, a structural unit (1a) based on a fluoroallyl ether compound represented by the following general formula (1a):

wherein each X is the same, and represents F or H; n5 represents 0 or an integer of 1 to 10; and A is as defined above, and is also preferably a structural unit (1A) based on a monomer represented by the following general formula (1A):

wherein Rf and A are as described above.

In the fluoropolymer, the proportion of carbon atom-bonded hydrogen atoms replaced with fluorine atoms is preferably 50% or more.

The fluoropolyrer preferably contains an ionic group, and preferably has an ion exchange rate of 53 or less.

In the fluoropolymer, the proportion of carbon atom-bonded hydrogen atoms replaced with fluorine atoms is preferably 50% or more.

The fluoropolyrer is preferably a water-soluble polymer.

In the first composition of the present disclosure, the content (concentration) of the fluoropolymer is not limited, and may be, for example, 0.1 to 10.0% by mass based on the composition.

The first composition of the present disclosure may be obtained by diluting or concentrating the composition obtained by the first production method of the present disclosure described above.

The first composition of the present disclosure may solely contain one fluoropolymer, or may contain two or more different fluoropolymers.

In the first composition of the present disclosure, the content of a compound having a molecular weight of 700 or more and 3,000 or less is 3.5% or less based on the fluoropolymer. Adjusting the content of the compound having a molecular weight of 700 or more and 3,000 or less within the above range results in excellent dispersibility. The content is preferably 3.0% or less, still more preferably 2.5% or less, further preferably 1.5% or less, particularly preferably 1.0% or less, and most preferably 0.6% or less. The lower limit of the content of the compound having a molecular weight of 700 or more and 3,000 or less is not limited, and is, for example, 0.01%.

The content of the compound having a molecular weight of 700 or more and 3,000 or less is a value calculated from the peak area of GPC.

The compound having a molecular weight of 700 or more and 3,000 or less is not limited, and encompasses all compounds having the above molecular weight.

In the first composition of the present disclosure, the content of a compound having a molecular weight of 400 or more and 3,000 or less is preferably 3.7% or less based on the fluoropolymer. Adjusting the content of the compound having a molecular weight of 400 or more and 3,000 or less within the above range results in even better dispersibility. The content is preferably 3.2% or less, still more preferably 2.7% or less, further preferably 1.7% or less, still further preferably 1.2% or less, particularly preferably 1.0% or less, and most preferably 0.6% or less. The lower limit of the content of the compound having a molecular weight of 400 or more and 3,000 or less is not limited, and is, for example, 0.01%.

The content of the compound having a molecular weight of 400 or more and 3,000 or less is a value calculated from the peak area of GPC.

The compound having a molecular weight of 400 or more and 3,000 or less is not limited, and encompasses all compounds having the above molecular weight.

In the first composition of the present disclosure, the content of a compound having a molecular weight of 700 or more and less than 10,000 is 5.0% or less based on the fluoropolymer. Adjusting the content of the compound having a molecular weight of 700 or more and less than 10,000 within the above range results in even better dispersibility. The content is preferably 4.0% or less, more preferably 2.0% or less, still more preferably 1.5% or less, particularly preferably 1.0% or less, and most preferably 0.6% or less. The lower limit of the content of the compound having a molecular weight of 700 or more and less than 10,000 is not limited, and is, for example, 0.01%.

The content of the compound having a molecular weight of 700 or more and less than 10,000 is a value calculated from the peak area of GPC.

The compound having a molecular weight of 700 or more and less than 10,000 is not limited, and encompasses all compounds having the above molecular weight.

In the first composition of the present disclosure, from the viewpoint of dispersibility, the content of the compound having a molecular weight of 700 or more and less than 3,000 is preferably 3.5% or less, more preferably 3.0% or less, still more preferably 2.5% or less, further preferably 2.0% or less, still further preferably 1.5% or less, particularly preferably 1.0% or less, and most preferably 0.6% or less, based on the fluoropolymer. The lower limit of the content of the compound having a molecular weight of 700 or more and less than 3,000 is not limited, and is, for example, 0.01%.

The content of the compound having a molecular weight of 700 or more and less than 3,000 is a value calculated from the peak area of GPC.

The compound having a molecular weight of 700 or more and less than 3,000 is not limited, and encompasses all compounds having the above molecular weight.

In the first composition of the present disclosure, from the viewpoint of dispersibility, the content of the compound having a molecular weight of 700 or more and less than 5,000 is preferably 4.0% or less, more preferably 3.5% or less, still more preferably 3.0% or less, further preferably 2.0% or less, still further preferably 1.5% or less, particularly preferably 1.0% or less, and most preferably 0.6% or less, based on the fluoropolymer. The lower limit of the content of the compound having a molecular weight of 700 or more and less than 5,000 is not limited, and is, for example, 0.01%.

The content of the compound having a molecular weight of 700 or more and less than 5,000 is a value calculated from the peak area of GPC.

The compound having a molecular weight of 700 or more and less than 5,000 is not limited, and encompasses all compounds having the above molecular weight.

In the first composition of the present disclosure, from the viewpoint of dispersibility, the content of the compound having a molecular weight of 700 or more and less than 20,000 is preferably 11.0% or less, more preferably 10.0% or less, still more preferably 9.0% or less, and particularly preferably 7.8% or less, based on the fluoropolymer. The lower limit of the content of the compound having a molecular weight of 700 or more and less than 20,000 is not limited, and is, for example, 0.01%. The content of the compound having a molecular weight of 700 or more and less than 20,000 is a value calculated from the peak area of GPC.

The compound having a molecular weight of 700 or more and less than 20,000 is not limited, and encompasses all compounds having the above molecular weight.

The first composition of the present disclosure may be used as-is, or may be used after being diluted or concentrated.

In addition, the fluoropolyrer after being separated from the first composition of the present disclosure may be used. For example, the fluoropolymer can be separated and used as a dispersant. The dispersant can be used, for example, when producing a polymer, and can be used as a dispersant that is added after a polymer is produced.

In particular, by polymerizing a fluoromonomer in the presence of the fluoropolymer obtained from the first composition of the present disclosure, a further fluoropolymer other than the above fluoropolymer can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (FVE), $CH_2=CFCF_3$, $CHF=CHCF_3$ (E form), $CHF=CHCF_3$ (Z form), or the like.

Examples of the further fluoropolymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro(alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further fluoropolymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The first composition of the present disclosure can be used as a coating agent. Since the content of a compound having a molecular weight of 700 or more and 3,000 or less is reduced, the first composition of the present disclosure has excellent dispersibility (property of dispersing other components).

When the first composition of the present disclosure is a coating agent, the composition may contain the further fluoropolymer, water, and the like.

The present disclosure also relates to a composition (hereinafter also referred to as the "second composition of the present disclosure") containing water and a polymer in which a proportion of carbon atom-bonded hydrogen atoms replaced with fluorine atoms is 50% or more, which contains an ionic group, and which has an ion-exchange rate of 53 or less (hereinafter also referred to as a "polymer α"), wherein the content of a compound having a molecular weight of 700 or more and 3,000 or less is 3.5% or less based on the polymer α.

The second composition of the present disclosure may be an aqueous solution.

In the second composition of the present disclosure, the content of a compound having a molecular weight of 400 or more and 3,000 or less is preferably 3.7% or less based on the polymer α.

Also, in the second composition of the present disclosure, the content of a compound having a molecular weight of 700 or more and less than 10,000 is preferably 5.0% or less based on the polymer α.

Due to the reduced amount of low molecular weight substance, the second composition of the present disclosure can improve dispersibility (property of dispersing other components) when used as a dispersant in a polymer dispersion.

The coating agent obtained from the second composition of the present disclosure has excellent transparency, water repellency, and antireflection properties.

The second composition of the present disclosure can be preferably produced by the second production method of the present disclosure.

The second composition of the present disclosure contains water. The water content is not limited, and is preferably such an amount that the fluoropolymer can be dispersed or dissolved.

Examples of the polymer α in the second composition of the present disclosure include what is described with respect to the second production method of the present disclosure. Also, suitable embodiments can all be adopted.

The polymer α is preferably a water-soluble polymer.

In the second composition of the present disclosure, the content of the polymer α is not limited, and may be, for example, 0.1 to 10.0% by mass based on the composition.

The second composition of the present disclosure may be obtained by diluting or concentrating the composition obtained by the second production method of the present disclosure described above.

The second composition of the present disclosure may solely contain one polymer α, or may contain two or more different polymers α.

In the second composition of the present disclosure, the content of a compound having a molecular weight of 700 or more and 3,000 or less is 3.5% or less based on the polymer α. Adjusting the content of the compound having a molecular weight of 700 or more and 3,000 or less within the above range results in excellent dispersibility. The content is preferably 3.0% or less, still more preferably 2.5% or less, further preferably 1.5% or less, particularly preferably 1.0% or less, and most preferably 0.6% or less. The lower limit of the content of the compound having a molecular weight of 700 or more and 3,000 or less is not limited, and is, for example, 0.01%.

The content of the compound having a molecular weight of 700 or more and 3,000 or less is a value calculated from the peak area of GPC.

The compound having a molecular weight of 700 or more and 3,000 or less is not limited, and encompasses all compounds having the above molecular weight.

In the second composition of the present disclosure, the content of a compound having a molecular weight of 400 or more and 3,000 or less is preferably 3.7% or less based on the polymer α. Adjusting the content of the compound having a molecular weight of 400 or more and 3,000 or less within the above range results in even better dispersibility. The content is preferably 3.2% or less, still more preferably 2.7% or less, further preferably 1.7% or less, still further preferably 1.2% or less, particularly preferably 1.0% or less, and most preferably 0.6% or less. The lower limit of the content of the compound having a molecular weight of 400 or more and 3,000 or less is not limited, and is, for example, 0.01%.

The content of the compound having a molecular weight of 400 or more and 3,000 or less is a value calculated from the peak area of GPC.

The compound having a molecular weight of 400 or more and 3,000 or less is not limited, and encompasses all compounds having the above molecular weight.

In the second composition of the present disclosure, the content of a compound having a molecular weight of 700 or more and less than 10,000 is preferably 5.0% or less based on the polymer α. Adjusting the content of the compound having a molecular weight of 700 or more and less than 10,000 within the above range results in even better dispersibility. The content is preferably 4.0% or less, more preferably 2.0% or less, still more preferably 1.5% or less, particularly preferably 1.0% or less, and most preferably 0.6% or less. The lower limit of the content of the compound having a molecular weight of 700 or more and less than 10,000 is not limited, and is, for example, 0.01%.

The content of the compound having a molecular weight of 700 or more and less than 10,000 is a value calculated from the peak area of GPC.

The compound having a molecular weight of 700 or more and less than 10,000 is not limited, and encompasses all compounds having the above molecular weight.

In the second composition of the present disclosure, from the viewpoint of dispersibility, the content of the compound having a molecular weight of 700 or more and less than 3,000 is preferably 3.5% or less, more preferably 3.0% or less, still more preferably 2.5% or less, further preferably 2.0% or less, still further preferably 1.5% or less, particularly preferably 1.0% or less, and most preferably 0.6% or less based on the polymer α. The lower limit of the content of the compound having a molecular weight of 700 or more and less than 3,000 is not limited, and is, for example, 0.01%.

The content of the compound having a molecular weight of 700 or more and less than 3,000 is a value calculated from the peak area of GPC.

The compound having a molecular weight of 700 or more and less than 3,000 is not limited, and encompasses all compounds having the above molecular weight.

In the second composition of the present disclosure, from the viewpoint of dispersibility, the content of the compound having a molecular weight of 700 or more and less than 5,000 is preferably 4.0% or less, more preferably 3.5% or less, still more preferably 3.0% or less, further preferably 2.0% or less, still further preferably 1.5% or less, particularly preferably 1.0% or less, and most preferably 0.6% or less based on the polymer α. The lower limit of the content of the compound having a molecular weight of 700 or more and less than 5,000 is not limited, and is, for example, 0.01%.

The content of the compound having a molecular weight of 700 or more and less than 5,000 is a value calculated from the peak area of GPC.

The compound having a molecular weight of 700 or more and less than 5,000 is not limited, and encompasses all compounds having the above molecular weight.

In the second composition of the present disclosure, from the viewpoint of dispersibility, the content of the compound having a molecular weight of 700 or more and less than 20,000 is preferably 11.0% or less, more preferably 10.0% or less, still more preferably 9.0% or less, and further preferably 7.8% or less based on the polymer α. The lower limit of the content of the compound having a molecular weight of 700 or more and less than 20,000 is not limited, and is, for example, 0.01%.

The content of the compound having a molecular weight of 700 or more and less than 20,000 is a value calculated from the peak area of GPC.

The compound having a molecular weight of 700 or more and less than 20,000 is not limited, and encompasses all compounds having the above molecular weight.

The second composition of the present disclosure may be used as-is, or may be used after being diluted or concentrated.

In addition, the polymer α after being separated from the second composition of the present disclosure may be used. For example, the polymer α can be separated and used as a dispersant. The dispersant can be used, for example, when producing a polymer, and can be used as a dispersant that is added after a polymer is produced.

In particular, by polymerizing a fluoromonomer in the presence of the polymer α obtained from the second composition of the present disclosure, a further polymer other than the polymer α can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (FVE), $CH_2=CFCF_3$, $CHF=CHCF_3$ (E form), $CHF=CHCF_3$ (Z form), or the like.

Examples of the further polymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro (alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further polymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The second composition of the present disclosure can be used as a coating agent. Since the content of a compound having a molecular weight of 700 or more and 3,000 or less is reduced, the second composition of the present disclosure has excellent dispersibility (property of dispersing other components).

When the second composition of the present disclosure is a coating agent, the composition may contain the further polymer, water, and the like.

The present disclosure also relates to a composition (hereinafter also referred to as the "third composition of the present disclosure") containing water and a water-soluble polymer in which a proportion of carbon atom-bonded hydrogen atoms replaced with fluorine atoms is 50% or more, wherein a content of a compound having a molecular weight of 700 or more and 3,000 or less is 3.5% or less based on the water-soluble polymer.

The third composition of the present disclosure may be an aqueous solution.

In the third composition of the present disclosure, the content of a compound having a molecular weight of 400 or more and 3,000 or less is preferably 3.7% or less based on the water-soluble polymer.

The content of a compound having a molecular weight of 700 or more and less than 10,000 is preferably 5.0% or less based on the water-soluble polymer.

Due to the reduced amount of low molecular weight substance, the third composition of the present disclosure can improve dispersibility (property of dispersing other components) when used as a dispersant in a polymer dispersion.

The coating agent obtained from the third composition of the present disclosure has excellent transparency, water repellency, and antireflection properties.

The third composition of the present disclosure can be preferably produced by the third production method of the present disclosure.

The third composition of the present disclosure contains water. The water content is not limited, and is preferably such an amount that the water-soluble polymer can be dispersed or dissolved, and preferably such an amount that the water-soluble polymer can be dissolved. Examples of the water-soluble polymer in the third composition of the present disclosure include what is described with respect to the third production method of the present disclosure. Also, suitable embodiments can all be adopted.

In the third composition of the present disclosure, the content of the water-soluble polymer is not limited, and may be, for example, 0.1 to 10.0% by mass based on the composition.

The third composition of the present disclosure may be obtained by diluting or concentrating the composition obtained by the third production method of the present disclosure described above.

The third composition of the present disclosure may solely contain one water-soluble polymer, or may contain two or more different water-soluble polymers.

In the third composition of the present disclosure, the content of the water-soluble polymer is not limited, and may be, for example, 0.1 to 10.0% by mass based on the composition.

The third composition of the present disclosure may be obtained by diluting or concentrating the composition obtained by the third production method of the present disclosure described above.

The third composition of the present disclosure may solely contain one water-soluble polymer, or may contain two or more different water-soluble polymers.

In the third composition of the present disclosure, the content of a compound having a molecular weight of 700 or more and 3,000 or less is 3.5% or less based on the water-soluble polymer. Adjusting the content of the compound having a molecular weight of 700 or more and 3,000 or less within the above range results in excellent dispersibility. The content is preferably 3.0% or less, still more preferably 2.5% or less, further preferably 1.5% or less, particularly preferably 1.0% or less, and most preferably 0.6% or less. The lower limit of the content of the compound having a molecular weight of 700 or more and 3,000 or less is not limited, and is, for example, 0.01%.

The content of the compound having a molecular weight of 700 or more and 3,000 or less is a value calculated from the peak area of GPC.

The compound having a molecular weight of 700 or more and 3,000 or less is not limited, and encompasses all compounds having the above molecular weight.

In the third composition of the present disclosure, the content of a compound having a molecular weight of 400 or more and 3,000 or less is preferably 3.7% or less based on the water-soluble polymer. Adjusting the content of the compound having a molecular weight of 400 or more and 3,000 or less within the above range results in even better dispersibility. The content is preferably 3.2% or less, and still more preferably 2.7% or less. The content is still more preferably 1.7% or less, further preferably 1.2% or less, particularly preferably 1.0% or less, and most preferably 0.6% or less. The lower limit of the content of the compound having a molecular weight of 400 or more and 3,000 or less is not limited, and is, for example, 0.01%.

The content of the compound having a molecular weight of 400 or more and 3,000 or less is a value calculated from the peak area of GPC.

The compound having a molecular weight of 400 or more and 3,000 or less is not limited, and encompasses all compounds having the above molecular weight.

In the third composition of the present disclosure, the content of a compound having a molecular weight of 700 or more and less than 10,000 is preferably 5.0% or less based on the water-soluble polymer. Adjusting the content of the compound having a molecular weight of 700 or more and less than 10,000 within the above range results in even better dispersibility. The content is preferably 4.0% or less, more preferably 2.0% or less, still more preferably 1.5% or less, particularly preferably 1.0% or less, and most preferably 0.6% or less. The lower limit of the content of the compound having a molecular weight of 700 or more and less than 10,000 is not limited, and is, for example, 0.01%.

The content of the compound having a molecular weight of 700 or more and less than 10,000 is a value calculated from the peak area of GPC.

The compound having a molecular weight of 700 or more and less than 10,000 is not limited, and encompasses all compounds having the above molecular weight.

In the third composition of the present disclosure, from the viewpoint of dispersibility, the content of the compound having a molecular weight of 700 or more and less than 3,000 is preferably 3.5% or less, more preferably 3.0% or less, still more preferably 2.5% or less, further preferably 2.0% or less, still further preferably 1.5% or less, particularly preferably 1.0% or less, and most preferably 0.6% or less based on the water-soluble polymer. The lower limit of the content of the compound having a molecular weight of 700 or more and less than 3,000 is not limited, and is, for example, 0.01%.

The content of the compound having a molecular weight of 700 or more and less than 3,000 is a value calculated from the peak area of GPC.

The compound having a molecular weight of 700 or more and less than 3,000 is not limited, and encompasses all compounds having the above molecular weight.

In the third composition of the present disclosure, from the viewpoint of dispersibility, the content of the compound having a molecular weight of 700 or more and less than 5,000 is preferably 4.0% or less, more preferably 3.5% or less, still more preferably 3.0% or less, further preferably 2.0% or less, still further preferably 1.5% or less, particularly preferably 1.0% or less, and most preferably 0.6% or less based on the water-soluble polymer. The lower limit of the content of the compound having a molecular weight of 700 or more and less than 5,000 is not limited, and is, for example, 0.01%.

The content of the compound having a molecular weight of 700 or more and less than 5,000 is a value calculated from the peak area of GPC. The compound having a molecular weight of 700 or more and less than 5,000 is not limited, and encompasses all compounds having the above molecular weight.

In the third composition of the present disclosure, from the viewpoint of dispersibility, the content of the compound having a molecular weight of 700 or more and less than 20,000 is preferably 11.0% or less, more preferably 10.0% or less, still more preferably 9.0% or less, and particularly preferably 7.8% or less based on the water-soluble polymer. The lower limit of the content of the compound having a molecular weight of 700 or more and less than 20,000 is not limited, and is, for example, 0.01%.

The content of the compound having a molecular weight of 700 or more and less than 20,000 is a value calculated from the peak area of GPC.

The compound having a molecular weight of 700 or more and less than 20,000 is not limited, and encompasses all compounds having the above molecular weight.

The third composition of the present disclosure may be used as-is, or may be used after being diluted or concentrated.

In addition, the water-soluble polymer after being separated from the third composition of the present disclosure may be used. For example, the water-soluble polymer can be separated and used as a dispersant. The dispersant can be used, for example, when producing a polymer, and can be used as a dispersant that is added after a polymer is produced.

In particular, by polymerizing a fluoromonomer in the presence of the water-soluble polymer obtained from the third composition of the present disclosure, a further polymer other than the water-soluble polymer can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (FVE), $CH_2$=$CFCF_3$, CHF=$CHCF_3$ (E form), CHF=$CHCF_3$ (Z form), or the like.

Examples of the further polymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro (alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further polymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The third composition of the present disclosure can be used as a coating agent. Since the content of a compound having a molecular weight of 700 or more and 3,000 or less is reduced, the third composition of the present disclosure has excellent dispersibility (property of dispersing other components).

When the third composition of the present disclosure is a coating agent, the composition may contain the further polymer, water, and the like.

The present disclosure also relates to a composition (hereinafter also referred to as the "fourth composition of the present disclosure") containing water and a fluoropolymer that is a polymer containing a structural unit M3 derived from a monomer represented by general formula (1):

$$CX_2=CY(-CZ_2-O-Rf-A) \quad (1)$$

wherein X is the same or different and is —H or —F; Y is —H, —F, an alkyl group, or a fluorine-containing alkyl group; Z is the same or different and is —H, —F, an alkyl group, or a fluoroalkyl group; Rf is a fluorine-containing alkylene group having 1 to 40 carbon atoms or a fluorine-containing alkylene group having 2 to 100 carbon atoms and having an ether bond; and A is —COOM, —$SO_3M$, —$OSO_3M$, or —$C(CF_3)_2OM$, wherein M is —H, a metal atom, —$NR^7_4$, imidazolium optionally having a substituent, pyridinium optionally having a substituent, or phosphonium optionally having a substituent, and $R^7$ is H or an organic group; provided that at least one of X, Y, and Z contains a fluorine atom, wherein a content of a dimer and a trimer of a monomer forming a structural unit constituting the fluoropolymer is 2.0% or less based on the fluoropolymer.

The fourth composition of the present disclosure may be an aqueous solution.

In the fourth composition of the present disclosure, the content of a dimer and a trimer is reduced, and thus by using the fourth composition of the present disclosure in the polymerization of a monomer in an aqueous medium, a polymer having a reduced content of the dimer and the trimer can be obtained.

The fourth composition of the present disclosure can be preferably produced by the first production method of the present disclosure.

In the fluoropolymer, the proportion of carbon atom-bonded hydrogen atoms replaced with fluorine atoms is preferably 50% or more.

The fluoropolymer preferably contains an ionic group and preferably has an ion exchange rate of 53 or less.

In the fluoropolymer, the proportion of carbon atom-bonded hydrogen atoms replaced with fluorine atoms is preferably 50% or more.

The fluoropolymer is preferably a water-soluble polymer.

The fourth composition of the present disclosure contains water. The water content is not limited, and is preferably such an amount that the fluoropolymer can be dispersed or dissolved.

Examples of the fluoropolymer in the fourth composition of the present disclosure include what is described with respect to the first production method of the present disclosure. Also, suitable embodiments can all be adopted.

In the fourth composition of the present disclosure, the content of the fluoropolymer is not limited, and may be, for example, 0.1 to 10.0% by mass based on the composition.

The fourth composition of the present disclosure may be obtained by diluting or concentrating the composition obtained by the first production method of the present disclosure described above.

The fourth composition of the present disclosure may solely contain one fluoropolymer, or may contain two or more different fluoropolymers.

In the fourth composition of the present disclosure, the dimer and the trimer are preferably a dimer and a trimer of the monomer represented by the general formula (I) (hereinafter, also referred to as a monomer (I)). The dimer and the trimer may be what is formed of, as the monomer (I) represented by the general formula (I), one monomer (I) or may be what is formed of two or more monomers (I) having different structures. As the monomer forming a suitable structural unit constituting the fluoropolymer, examples of the dimer and trimer include a dimer and a trimer of the above-described monomer.

The content of the dimer and the trimer in the fourth composition of the present disclosure is, in order of preference, 2.0% or less, 1.5% or less, 1.0% or less, 0.1% or less, 0.01% or less, 0.001% or less, and 0.0001% or less based on the fluoropolymer.

The method for measuring the content of the dimer and the trimer in the composition is as described above.

In the fourth composition of the present disclosure, the content of the compound having a molecular weight of 700 or more and less than 1,000 is preferably 2.0% or less, more preferably 1.5% or less, still more preferably 1.0% or less, and further preferably 0.6% or less based on the fluoropolymer. The lower limit of the content of the compound having a molecular weight of 700 or more and less than 1,000 is not limited, and is, for example, 0.01%.

In the fourth composition of the present disclosure, the content of the compound having a molecular weight of 700 or more and 3,000 or less is preferably 3.5% or less, more preferably 3.0% or less, still more preferably 2.5% or less, further preferably 1.5% or less, particularly preferably 1.0% or less, and most preferably 0.6% or less based on the fluoropolymer. The lower limit of the content of the compound having a molecular weight of 700 or more and 3,000 or less is not limited, and is, for example, 0.01%.

In the fourth composition of the present disclosure, the content of the compound having a molecular weight of 400 or more and 3,000 or less is preferably 3.7% or less, more preferably 3.2% or less, still more preferably 2.7% or less, further preferably 1.7% or less, still further preferably 1.2% or less, particularly preferably 1.0% or less, and most preferably 0.6% or less based on the fluoropolymer. The lower limit of the content of the compound having a molecular weight of 400 or more and 3,000 or less is not limited, and is, for example, 0.01%.

The content of the compound having a molecular weight of 700 or more and less than 1,000, the compound having a molecular weight of 700 or more and 3,000 or less, and the compound having a molecular weight of 400 or more and 3,000 or less is a value calculated from the peak area of GPC.

The compound having a molecular weight of 700 or more and less than 1,000, the compound having a molecular weight of 700 or more and 3,000 or less, and the compound having a molecular weight of 400 or more and 3,000 or less are not limited, and encompass all compounds having the above molecular weight.

In particular, by polymerizing a fluoromonomer in the presence of the fluoropolymer obtained from the fourth composition of the present disclosure, a further polymer other than the above fluoropolymer can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (EVE), $CH_2=CFCF_3$, $CHF=CHCF_3$ (E form), $CHF=CHCF_3$ (Z form), or the like.

Examples of the further polymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro (alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further polymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The fourth composition of the present disclosure can be used as a coating agent. When the fourth composition of the present disclosure is a coating agent, the composition may contain the further polymer, water, and the like.

The present disclosure also relates to a composition (hereinafter also referred to as the "fifth composition of the present disclosure") containing a polymer α in which a proportion of carbon atom-bonded hydrogen atoms replaced with fluorine atoms is 50% or more, which contains an ionic group, and which has an ion-exchange rate of 53 or less, wherein a content of a dimer and a trimer of a monomer forming a structural unit constituting the polymer α is 2.0% or less based on the polymer α.

The fifth composition of the present disclosure may be an aqueous solution.

In the fifth composition of the present disclosure, the content of a dimer and a trimer is reduced, and thus by using the fifth composition of the present disclosure in the polymerization of a monomer in an aqueous medium, a polymer having a reduced content of the dimer and the trimer can be obtained.

The fifth composition of the present disclosure can be preferably produced by the second production method of the present disclosure.

The fifth composition of the present disclosure contains water. The water content is not limited, and is preferably such an amount that the polymer α can be dispersed or dissolved.

Examples of the polymer α in the fifth composition of the present disclosure include what is described with respect to the second production method of the present disclosure. Also, suitable embodiments can all be adopted.

The polymer α is preferably a water-soluble polymer.

In the fifth composition of the present disclosure, the content of the polymer α is not limited, and may be, for example, 0.1 to 10.0% by mass based on the composition.

The fifth composition of the present disclosure may be obtained by diluting or concentrating the composition obtained by the second production method of the present disclosure described above.

The fifth composition of the present disclosure may solely contain one polymer α, or may contain two or more different polymers α.

In the fifth composition of the present disclosure, the dimer and the trimer are preferably a dimer and a trimer of the monomer represented by the general formula (I) (hereinafter, also referred to as a monomer (I)). The dimer and the trimer may be what is formed of, as the monomer (I) represented by the general formula (I), one monomer (I) or may be what is formed from two or more monomers (I) having different structures. As the monomer forming a suitable structural unit constituting the polymer α, examples of the dimer and trimer include a dimer and a trimer of the above-described monomer.

The content of the dimer and the trimer in the fifth composition of the present disclosure is, in order of preference, 2.0% or less, 1.5% or less, 1.0% or less, 0.1% or less, 0.01% or less, 0.001% or less, and 0.0001% or less based on the polymer α.

The method for measuring the content of the dimer and the trimer in the composition is as described above.

In the fifth composition of the present disclosure, the content of the compound having a molecular weight of 700 or more and less than 1,000 is preferably 2.0% or less, more preferably 1.5% or less, still more preferably 1.0% or less, and further preferably 0.6% or less based on the polymer α. The lower limit of the content of the compound having a molecular weight of 700 or more and less than 1,000 is not limited, and is, for example, 0.01%.

In the fifth composition of the present disclosure, the content of the compound having a molecular weight of 700 or more and 3,000 or less is preferably 3.5% or less, more preferably 3.0% or less, still more preferably 2.5% or less, further preferably 1.5% or less, particularly preferably 1.0% or less, and most preferably 0.6% or less based on the polymer α. The lower limit of the content of the compound having a molecular weight of 700 or more and 3,000 or less is not limited, and is, for example, 0.01%.

In the fifth composition of the present disclosure, the content of the compound having a molecular weight of 400 or more and 3,000 or less is preferably 3.7% or less, more preferably 3.2% or less, still more preferably 2.7% or less, further preferably 1.7% or less, still further preferably 1.2% or less, particularly preferably 1.0% or less, and most preferably 0.6% or less based on the polymer α. The lower limit of the content of the compound having a molecular weight of 400 or more and 3,000 or less is not limited, and is, for example, 0.01%.

The content of the compound having a molecular weight of 700 or more and less than 1,000, the compound having a molecular weight of 700 or more and 3,000 or less, and the compound having a molecular weight of 400 or more and 3,000 or less is a value calculated from the peak area of GPC.

The compound having a molecular weight of 700 or more and less than 1,000, the compound having a molecular weight of 700 or more and 3,000 or less, and the compound having a molecular weight of 400 or more and 3,000 or less are not limited, and encompass all compounds having the above molecular weight.

In particular, by polymerizing a fluoromonomer in the presence of the polymer α obtained from the fifth composition of the present disclosure, a further polymer other than the polymer α can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (EVE), $CH_2=CFCF_3$, $CHF=CHCF_3$ (E form), $CHF=CHCF_3$ (Z form), or the like.

Examples of the further polymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro (alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further polymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The fifth composition of the present disclosure can be used as a coating agent. When the fifth composition of the present disclosure is a coating agent, the composition may contain the further polymer, water, and the like.

The present disclosure also relates to a composition (hereinafter also referred to as the "sixth composition of the present disclosure") containing water and a water-soluble polymer in which a proportion of carbon atom-bonded hydrogen atoms replaced with fluorine atoms is 50% or more, wherein a content of a dimer and a trimer of a monomer forming a structural unit constituting the water-soluble polymer is 2.0% or less based on the water-soluble polymer.

The sixth composition of the present disclosure may be an aqueous solution.

In the sixth composition of the present disclosure, the content of a dimer and a trimer is reduced, and thus by using the sixth composition of the present disclosure in the polymerization of a monomer in an aqueous medium, a polymer having a reduced content of the dimer and the trimer can be obtained.

The sixth composition of the present disclosure can be preferably produced by the third production method of the present disclosure.

The sixth composition of the present disclosure contains water. The water content is not limited, and is preferably such an amount that the water-soluble polymer can be dispersed or dissolved, and preferably such an amount that the water-soluble polymer can be dissolved.

Examples of the water-soluble polymer in the sixth composition of the present disclosure include what is described with respect to the third production method of the present disclosure. Also, suitable embodiments can all be adopted.

In the sixth composition of the present disclosure, the content of the water-soluble polymer is not limited, and may be, for example, 0.1 to 10.0% by mass based on the composition.

The sixth composition of the present disclosure may be obtained by diluting or concentrating the composition obtained by the third production method of the present disclosure described above.

The sixth composition of the present disclosure may solely contain one water-soluble polymer, or may contain two or more different water-soluble polymers.

In the sixth composition of the present disclosure, the dimer and the trimer are preferably a dimer and a trimer of the monomer represented by the general formula (I) (hereinafter, also referred to as a monomer (I)). The dimer and the trimer may be what is formed of, as the monomer (I) represented by the general formula (I), one monomer (I) or may be what is formed of two or more monomers (I) having different structures. As the monomer forming a suitable structural unit constituting the water-soluble polymer, examples of the dimer and the trimer include a dimer and a trimer of the above-described monomer.

The content of the dimer and the trimer in the sixth composition of the present disclosure is, in order of preference, 2.0% or less, 1.5% or less, 1.0% or less, 0.1% or less, 0.01% or less, 0.001% or less, and 0.0001% or less based on the water-soluble polymer.

The method for measuring the content of the dimer and the trimer in the composition is as described above.

In the sixth composition of the present disclosure, the content of the compound having a molecular weight of 700 or more and less than 1,000 is preferably 2.0% or less, more preferably 1.5% or less, still more preferably 1.0% or less, and further preferably 0.6% or less based on the water-soluble polymer. The lower limit of the content of the compound having a molecular weight of 700 or more and less than 1,000 is not limited, and is, for example, 0.01%.

In the sixth composition of the present disclosure, the content of the compound having a molecular weight of 700 or more and 3,000 or less is preferably 3.5% or less, more preferably 3.0% or less, still more preferably 2.5% or less, further preferably 1.5% or less, particularly preferably 1.0% or less, and most preferably 0.6% or less based on the water-soluble polymer. The lower limit of the content of the compound having a molecular weight of 700 or more and 3,000 or less is not limited, and is, for example, 0.01%.

In the sixth composition of the present disclosure, the content of the compound having a molecular weight of 400 or more and 3,000 or less is preferably 3.7% or less, more preferably 3.2% or less, still more preferably 2.7% or less, further preferably 1.7% or less, still further preferably 1.2% or less, particularly preferably 1.0% or less, and most preferably 0.6% or less based on the water-soluble polymer. The lower limit of the content of the compound having a molecular weight of 400 or more and 3,000 or less is not limited, and is, for example, 0.01%.

The content of the compound having a molecular weight of 700 or more and less than 1,000, the compound having a molecular weight of 700 or more and 3,000 or less, and the compound having a molecular weight of 400 or more and 3,000 or less is a value calculated from the peak area of GPC.

The compound having a molecular weight of 700 or more and less than 1,000, the compound having a molecular weight of 700 or more and 3,000 or less, and the compound having a molecular weight of 400 or more and 3,000 or less are not limited, and encompass all compounds having the above molecular weight.

In particular, by polymerizing a fluoromonomer in the presence of the water-soluble polymer obtained from the sixth composition of the present disclosure, a further polymer other than the water-soluble polymer can be produced.

The fluoromonomer is not limited as long as it is a monomer having at least one fluorine atom or fluoroalkyl group, and may contain, for example, trifluoroethylene, tetrafluoroethylene (TFE), vinylidene fluoride (VdF), vinyl fluoride (VF), chlorotrifluoroethylene (CTFE), hexafluoropropylene (HFP), hexafluoroisobutylene, perfluoroalkylethylene, fluorovinyl ether (FVE), $CH_2\!=\!CFCF_3$, $CHF\!=\!CHCF_3$ (E form), $CHF\!=\!CHCF_3$ (Z form), or the like.

Examples of the further polymer include polytetrafluoroethylene (PTFE), copolymers of TFE with another monomer copolymerizable with TFE (fluorine-containing monomers such as vinylidene fluoride, hexafluoropropylene, chlorotrifluoroethylene, and perfluoro(alkyl vinyl ether), hydrocarbon olefins such as ethylene, propylene, and isobutene, and alkyl vinyl ether,) (e.g., a tetrafluoroethylene-hexafluoropropylene copolymer (FEP), a tetrafluoroethylene-perfluoro (alkyl vinyl ether) copolymer (PFA), and an ethylene-tetrafluoroethylene copolymer (ETFE)), fluororesins such as polyvinylidene fluoride (PVDF), polychlorotrifluoroethylene (PCTFE), and ethylene-chlorotrifluoroethylene (ECTFE), vinylidene fluoride rubbers (FKM) such as a vinylidene fluoride-hexafluoropropylene copolymer, fluororubbers such as tetrafluoroethylene-propylene rubber (FEPM) and tetrafluoroethylene-perfluoromethyl vinyl ether rubber (FEKM), and fluorine-containing elastomers.

The PTFE may be a homopolymer of TFE, or may be modified PTFE containing 99.0% by mass or more of TFE and 1.0% by mass or less of a modifying monomer.

The further polymer is preferably at least one selected from the group consisting of PTFE and a melt-processable fluororesin containing 60.0 to 98.0% by mass of a TFE unit and 2.0 to 40.0% by mass of another monomer, and is particularly preferably PTFE.

The sixth composition of the present disclosure can be used as a coating agent. When the sixth composition of the present disclosure is a coating agent, the composition may contain the further polymer, water, and the like.

Although the embodiments have been described above, it will be understood that various changes in form and details are possible without departing from the gist and scope of the claims.

EXAMPLES

The production method of the present disclosure is described with reference to experimental examples, but the production method of the present disclosure is not intended to be limited by these experimental examples.

The numerical values of the experimental examples were measured by the following methods.

Method for measuring weight average molecular weight (Mw), number average molecular weight (Mn), and content of low molecular weight substance having molecular weight of 700 or more and 3,000 or less, low molecular weight substance having molecular weight of 400 or more and 3,000 or less, and low molecular weight substance having molecular weight of 700 or more and less than 10,000

The Mw and Mn of a fluoropolymer (a water-soluble polymer) and the content of a low molecular weight substance of 700 or more and less than 10,000 were obtained by calculating a molecular weight by gel permeation chromatography (GPC) using monodisperse polyethylene oxide (PEO) and polyethylene glycol (PEG) manufactured by Tosoh Corporation and Agilent as standards.

Method for measuring contents of dimers and trimers in polymers (such as polymers E and F)

(1) Extraction from Aqueous Solution

The concentration of an aqueous solution of a polymer was measured, and the amount of the aqueous solution corresponding to 0.2 g of the solid content of the polymer was weighed. Thereafter, water and methanol were added such that the volume ratio of water, including the water contained in the aqueous solution, to methanol was 50/50 (vol %) to obtain a mixed solution containing the polymer, water, and methanol. Thereafter, the obtained mixed solution was centrifuged at 4,000 rpm for 1 hour, and the supernatant containing the polymer was recovered as an extract.

The extract was analyzed using a liquid chromatograph-mass spectrometer (Waters, LC-MS ACQUITY UPLC/TQD) to obtain a chromatogram of the extract.

The content of a dimer and a trimer of a monomer contained in the extract was obtained by converting the integral values of peaks derived from the dimer and the trimer of the monomer appearing in the chromatogram of the extract into the contents of the dimer and the trimer of the monomer using a calibration curve.

(2) Calibration Curve of Monomer

Five concentration levels of a methanol standard solution of a monomer having a known content of 1 ng/mL to 100 ng/mL were prepared, and measurement was made using a liquid chromatograph-mass spectrometer (Waters, LC-MS ACQUITY UPLC/TQD). The relationship between the content of each monomer and the integrated value of a peak corresponding to the content was plotted to create a calibration curve (first-order approximation) of each monomer. Next, the calibration curve (first-order approximation) of each monomer was used to create calibration curves of a dimer and a trimer of each monomer.

Measuring Instrument Configuration and LC-MS Measurement Conditions

TABLE 1

| | LC unit |
|---|---|
| Equipment | Acquity UPLC manufactured by Waters |
| Column | Acquity UPLC BEH C18 1.7 mm (2.1 × 50 mm) manufactured by Waters |
| Mobile phase | A $CH_3CN$ |
| | B 20 mM $CH_3COONH_4/H_2O$ |
| | 0 → 1.5 min    A:B = 10:90 |
| | 1.5 → 8.5 min  A:B = 10:90 → A:B = 90:10 Linear gradient |
| | 8.5 → 10 min   A:B = 90:10 |
| Flow rate | 0.4 mL/min |
| Column temperature | 40° C. |
| Sample injection amount | 5 μL |
| | MS unit |
| Equipment | TQ Detector |
| Measurement mode | MRM (Multiple Reaction Monitoring) |
| Ionization method | Electrospray ionization |
| | SCAN |

The quantification limit in this measuring instrument configuration is 1 ng/mL.

Concentration (Solid Concentration) of Aqueous Polymer Solution

In a reduced-pressure dryer, about 1 g of an aqueous polymer solution was dried at 60° C. for 60 minutes, the mass of the non-volatile matter was measured, and the ratio of the mass of the non-volatile matter to the mass of the aqueous polymer solution (1 g) was expressed in percentage and taken as the solid concentration thereof.

Synthesis Example 1

First, 140 g of a monomer represented by $CH_2=CFCF_2OCF(CF_3)COOH$, 260 g of water, and APS (0.5 mol %) were added, and the mixture was heated and stirred at 60° C. for 17 hours in a nitrogen atmosphere to obtain an aqueous fluoropolymer solution A-1 containing a fluoropolymer that is a homopolymer of $CH_2=CFCF_2OCF(CF_3)COOH$. As a result of GPC analysis, the fluoropolymer had a Mw of 320,000 and a Mn of 100,000, and the content of a low molecular weight substance having a molecular weight of 700 or more and less than 10,000 was 7.1% based on the fluoropolymer. The content of a low molecular weight substance having a molecular weight of 700 or more and 3,000 or less was 3.7% based on the fluoropolymer. The content of a low molecular weight substance having a molecular weight of 400 or more and 3,000 or less was 3.9% based on the fluoropolymer.

Experimental Example 1

Water was added to the aqueous fluoropolymer solution A-1 to adjust the fluoropolymer concentration to 2.0% by mass, and then ultrafiltration was carried out using an ultrafiltration membrane (a molecular weight cut-off of 50,000 Da). While suitably adding water, ultrafiltration was carried out. As a result of GPC analysis of the aqueous solution after ultrafiltration, the fluoropolymer had a Mw of 360,000 and a Mn of 140,000, and the content of a low molecular weight substance having a molecular weight of 700 or more and less than 10,000 was 0.7% based on the fluoropolymer. Thus, it was found that the present method was effective for removing a low molecular weight substance. The content of a low molecular weight substance having a molecular weight of 700 or more and 3,000 or less was 0.6% or less based on the fluoropolymer. The content of a low molecular weight substance having a molecular weight of 400 or more and 3,000 or less was 0.6% or less based on the fluoropolyrer.

Experimental Example 2

Water was added to the aqueous fluoropolymer solution A-1 to prepare an aqueous solution (solid content 35 g) having a fluoropolyrer concentration of 2.0% by mass, 50 g of 10% hydrochloric acid was added to the aqueous solution to precipitate the fluoropolymer, an acetone solution of the precipitated fluoropolymer was poured into n-hexane, followed by separation and vacuum drying, and thus 34.7 g of a colorless, transparent polymer was obtained. As a result of GPC analysis of the resulting polymer, the fluoropolymer had a Mw of 350,000 and a Mn of 130,000, and the content of a low molecular weight substance having a molecular weight of 700 or more and less than 10,000 was 6.8% based on the fluoropolyrer. The content of a low molecular weight substance having a molecular weight of 700 or more and 3,000 or less was 3.6% based on the fluoropolymer. The content of a low molecular weight substance having a molecular weight of 400 or more and 3000 or less was 3.8% based on the fluoropolymer.

Thus, it was found that a low molecular weight substance can be barely removed by a conventional method in which a fluoropolymer is precipitated and recovered from an aqueous solution.

Synthesis Example 2

First, 10 g of a monomer E represented by $CF_2=CFOCF_2CF_2COOH$, 30 g of water, and APS (6.0 mol % based on the monomer E) were added to a reactor, and the mixture was heated and stirred at 80° C. for 23 hours in a nitrogen atmosphere to obtain a polymer E aqueous solution E-1 containing a polymer E that is a homopolymer of $CF_2=CFOCF_2CF_2COOH$. As a result of GPC analysis of the resulting polymer E aqueous solution E-1, the polymer E had a Mw of 7,000 and a Mn of 5,000. The content of a low molecular weight substance having a molecular weight of 700 or more and 3,000 or less was 4.6% based on the fluoropolymer. The content of a low molecular weight substance having a molecular weight of 400 or more and 3,000 or less was 4.6% based on the fluoropolymer.

Experimental Example 3

Water was added to the resulting polymer E aqueous solution E-1, and the aqueous solution was brought into contact with a dialysis membrane (a molecular weight cut-off of 35,000 Da, made of polyethylene) at 30° C. to carry out filtration, and thus a polymer E aqueous solution E-2 was obtained. As a result of GPC analysis and LC-MS analysis of the resulting polymer E aqueous solution E-2, the polymer E had a Mw of 7,000, a Mn of 6,000, and a content of the dimer and the trimer of less than 1 mass ppm based on the polymer E. The concentration of the resulting polymer E aqueous solution E-2 was 3.6% by mass. The content of a low molecular weight substance having a molecular weight of 700 or more and 3,000 or less was 0.05% or less based on the fluoropolymer. The content of a low molecular weight substance having a molecular weight of 400 or more and 3,000 or less was 0.05% or less based on the fluoropolymer.

Synthesis Example 3

First, 4.1 g of a monomer F represented by $CF_2=CFOCF_2CF(CF_3)OCF_2COOH$, 5.2 g of $CF_2=CF_2$, and APS (8.8 mol % based on the monomer F) were added, and the mixture was heated and stirred at 80° C. for 7 hours in a nitrogen atmosphere to obtain a polymer F aqueous solution F-1 containing a copolymer (polymer F) of the monomer F represented by $CF_2=CFOCF_2CF(CF_3)OCF_2COOH$ and $CF_2=CF_2$. As a result of GPC analysis of the resulting polymer F aqueous solution F-1, the polymer F had a Mw of 7,000 and a Mn of 4,000. The content of a low molecular weight substance having a molecular weight of 700 or more and 3,000 or less was 4.5% based on the fluoropolymer. The content of a low molecular weight substance having a molecular weight of 400 or more and 3,000 or less was 4.6% based on the fluoropolymer.

Experimental Example 4

The resulting polymer F aqueous solution F-1 was brought into contact with a dialysis membrane (a molecular weight cut-off of 35,000 Da, made of polyethylene) at 30° C. to carry out filtration, and thus a polymer F aqueous solution F-2 was obtained. As a result of GPC analysis and LC-MS analysis of the resulting polymer F aqueous solution F-2, the polymer F had a Mw of 9,000, a Mn of 6,000, and a content of the dimer and the trimer of less than 1 mass ppm based on the polymer F. The concentration of the resulting polymer F aqueous solution F-2 was 2.0% by mass. The content of a low molecular weight substance having a molecular weight of 700 or more and 3,000 or less was 0.05% or less based on the fluoropolymer. The content of a low molecular weight substance having a molecular weight of 400 or more and 3,000 or less was 0.05% or less based on the fluoropolymer.

Synthesis Example 3

First, 10 g of a monomer E represented by $CF_2=CFOCF_2CF_2COOH$, 30 g of water, and APS (2.5 mol % separation based on the monomer E) were added to a reactor, and the mixture was heated and stirred at 50° C. for 76 hours in a nitrogen atmosphere to obtain a polymer E aqueous solution E-1 containing a polymer E that is a homopolymer of $CF_2=CFOCF_2CF_2COOH$. As a result of GPC analysis and LC-MS analysis of the resulting polymer E aqueous solution E-1, the polymer E had a Mw of 13,000 and a Mn of 8,000. The content of a low molecular weight substance having a molecular weight of 700 or more and 3,000 or less was 3.9% based on the fluoropolymer. The content of a low molecular weight substance having a molecular weight of 400 or more and 3,000 or less was 4.0% based on the fluoropolymer.

Experimental Example 5

Water was added to the resulting polymer E aqueous solution E-1, and the aqueous solution was brought into contact with a dialysis membrane (a molecular weight cut-off of 35,000 Da, made of polyethylene) at 30° C. to carry out filtration, and thus a polymer E aqueous solution E-2 was obtained. As a result of GPC analysis and LC-MS analysis of the resulting polymer E aqueous solution E-2, the polymer E had a Mw of 13,000, a Mn of 10,000, and a content of the dimer and the trimer of less than 1 mass ppm based on the polymer E. The concentration of the resulting polymer E aqueous solution E-2 was 3.5% by mass. The content of a low molecular weight substance having a molecular weight of 700 or more and 3,000 or less was 0.05% or less based on the fluoropolymer. The content of a low molecular weight substance having a molecular weight of 400 or more and 3,000 or less was 0.05% or less based on the fluoropolymer.

The invention claimed is:

1. A method for producing a composition, the method comprising a step A of performing ultrafiltration, microfiltration, dialysis membrane treatment, or a combination thereof on a composition comprising water and a water-soluble fluoropolymer, wherein the fluoropolymer is a polymer comprising a structural unit M3 derived from a monomer represented by general formula (1):

$$CX_2=CY(-CZ_2-O-Rf-A) \qquad (1)$$

wherein
X is the same or different and is —H or —F;
Y is —H, —F, an alkyl group, or a fluorine-containing alkyl group;
Z is the same or different and is —H, —F, an alkyl group, or a fluoroalkyl group;

Rf is a fluorine-containing alkylene group having 1 to 40 carbon atoms or a fluorine-containing alkylene group having 2 to 100 carbon atoms and having an ether bond; and A is —COOM, —SO$_3$M, —OSO$_3$M, or —C(CF$_3$)$_2$OM, wherein M is —H, a metal atom, —NR$^7_4$, imidazolium optionally having a substituent, pyridinium optionally having a substituent, or phosphonium optionally having a substituent, and R$^7$ is H or an organic group;

provided that at least one of X, Y, and Z comprises a fluorine atom, wherein a content of the structural unit M3 in the fluoropolymer is 60 mol % or more based on all polymerization units.

2. The production method according to claim 1, wherein in the general formula (1), at least one X is —H.

3. The production method according to claim 1, wherein in the general formula (1), both X are —H.

4. The production method according to claim 1, wherein in the general formula (1), Rf is a fluorine-containing alkylene group having 1 to 10 carbon atoms or a fluorine-containing alkylene group having 2 to 12 carbon atoms and having an ether bond.

5. The production method according to claim 1, wherein the structural unit M3 is a structural unit (1A) based on a monomer represented by the following general formula (1A):

CH$_2$=CF(—CF$_2$—O—Rf-A)    (1A)

wherein Rf and A are as described above.

6. The production method according to claim 1, wherein the structural unit M3 is a structural unit (1a) based on a fluoroallyl ether compound represented by the following general formula (1a):

CX$_2$=CFCF$_2$—O—(CF(CF$_3$)CF$_2$O)$_{n5}$—CF(CF$_3$)-A    (1a)

wherein each X is the same and represents F or H; n5 represents 0 or an integer of 1 to 10; and A is as defined above.

7. The production method according to claim 1, wherein A is —COOM.

8. The production method according to claim 1, wherein M is —H, —Na, —K, —Li, or —NH$_4$.

9. The production method according to claim 1, wherein the fluoropolymer is a polymer in which a structural unit N3 derived from a monomer copolymerizable with the monomer represented by the general formula (1) is 0 to 40 mol % based on all polymerization units.

10. The production method according to claim 9, wherein the structural unit N3 is a structural unit derived from tetrafluoroethylene.

11. The production method according to claim 1, wherein the fluoropolymer is a polymer having a number average molecular weight of 0.5×10$^4$ to 75.0×10$^4$.

12. The production method according to claim 1, wherein the fluoropolymer is a polymer in which a proportion of carbon atom-bonded hydrogen atoms replaced with fluorine atoms is 50% or more, which comprises an ionic group, and which has an ion exchange rate of 53 or less.

13. The production method according to claim 1, wherein a proportion of carbon atom-bonded hydrogen atoms replaced with fluorine atoms in the fluoropolymer is 50% or more.

14. The production method according to claim 1, wherein the ultrafiltration, the microfiltration, or the dialysis membrane treatment is performed at a temperature of 20° C. or higher.

15. The production method according to claim 1, wherein the ultrafiltration is performed using an ultrafiltration membrane having a molecular weight cut-off of 1.5×10$^4$ Da or more.

* * * * *